(12) United States Patent
Vuyisich et al.

(10) Patent No.: US 12,100,479 B2
(45) Date of Patent: Sep. 24, 2024

(54) SYSTEMS AND METHODS FOR METAGENOMIC ANALYSIS

(71) Applicants: BlueDot LLC, Bellevue, WA (US); TRIAD NATIONAL SECURITY, LLC, Los Alamos, NM (US)

(72) Inventors: Momchilo Vuyisich, Los Alamos, NM (US); Jason Gans, Los Alamos, NM (US); Niels Klitgord, Poway, CA (US); Po-E Li, Los Alamos, NM (US); Patrick Chain, Los Alamos, NM (US)

(73) Assignees: BLUEDOT, LLC, Bellevue, WA (US); TRIAD NATIONAL SECURITY, LLC, Los Alamos, NM (US)

( * ) Notice: Subject to any disclaimer, the term of this patent is extended or adjusted under 35 U.S.C. 154(b) by 956 days.

(21) Appl. No.: 16/490,288

(22) PCT Filed: Mar. 1, 2018

(86) PCT No.: PCT/US2018/020539
§ 371 (c)(1),
(2) Date: Aug. 30, 2019

(87) PCT Pub. No.: WO2018/160899
PCT Pub. Date: Sep. 7, 2018

(65) Prior Publication Data
US 2020/0234793 A1  Jul. 23, 2020

Related U.S. Application Data

(60) Provisional application No. 62/465,747, filed on Mar. 1, 2017.

(51) Int. Cl.
*G16B 20/20* (2019.01)
*C12N 15/10* (2006.01)
*C12Q 1/6874* (2018.01)
*G16B 10/00* (2019.01)
*G16B 30/10* (2019.01)
*G16B 30/20* (2019.01)

(52) U.S. Cl.
CPC ......... *G16B 20/20* (2019.02); *C12N 15/1096* (2013.01); *C12Q 1/6874* (2013.01); *G16B 10/00* (2019.02); *G16B 30/10* (2019.02); *G16B 30/20* (2019.02)

(58) Field of Classification Search
CPC .... G16B 30/00; G16B 30/10; C12N 15/1096; C12Q 1/6874
See application file for complete search history.

(56) References Cited

U.S. PATENT DOCUMENTS

2012/0004111 A1  1/2012  Colwell et al.
2013/0121968 A1  5/2013  Quay
2014/0249036 A1  9/2014  Fry et al.
2016/0376627 A1  12/2016  Zengler et al.
2018/0365375 A1*  12/2018  Flygare .................. G16B 30/10

FOREIGN PATENT DOCUMENTS

WO  2016162504 A1  10/2016

OTHER PUBLICATIONS

Junemann, S. et al., Bacterial Community Shift in Treated Periodontitis Patients Revealed by Ion Torrent 16S rRNA Gene Amplicon Sequencing, PLOS One, vol. 7, e41606, pp. 1-8 (Year: 2012).*
Franzosa, E.A. et al., Relating the metatranscriptosome and metagenome of the human gut, PNAS, vol. 111, pp. E2329-E2338 (Year: 2014).*
Freitas, T.A.K. et al., Accurate read-based metagenomic characterization using a hierarchical suite of unique signatures, Nucl. Acids Res., vol. 43, e69, pp. 1-14 (Year: 2015).*
TruSeq RNA Sample Preparation v2 Guide, Part # 15026495 Rev. F, Published Mar. 2014, Illumina (Year: 2014).*
Freitas, T.A.K. et al., Accurate read-based metagenomic characterization using a hierarchical suite of unique signatures, Nucl. Acids Res.,2015; vol. 43, e69, pp. 1-14 (Year: 2015).*
Gardner, Shea N., et al. "Searching more genomic sequence with less memory for fast and accurate metagenomic profiling." bioRxiv (2016): 036681 (Year: 2016).*
Freitas et al., Accurate read-based metagenomic characterization using a hierarchical suite of unique signatures, Nucl. Acids Res. (2015), vol. 43, e69, pp. 1-14 (Year: 2015).*
Gardner et al., "Searching more genomic sequence with less memory for fast and accurate metagenomic profiling." bioRxiv (2016): 036681. (Year: 2016).*
Innocenti, Nicolas. Data Analysis and Next Generation Sequencing: Applications in Microbiology. Diss. KTH Royal Institute of Technology, 2015. (Year: 2015).*
Güllert et al. Deep metagenome and metatranscriptome analyses of microbial communities affiliated with an industrial biogas fermenter, a cow rumen, and elephant feces reveal major differences in carbohydrate hydrolysis strategies. Biotechnol Biofuels 9, 121 (2016) (Year: 2016).*
European Patent Office (EPO), International Search Report and Wrriten Opinion for PCT/US18/20539 dated May 23, 2018.
EUROPEAN Office Action for EP18711458.2 dated Sep. 29, 2022, 9 pages.
Yanmei, Shi et al. Integrated metatranscriptomic and metagenomic analyses of stratified microbial assemblages in the open ocean, The ISME Journal, vol. 5, No. 6. Dec. 9, 2010.
Shi, Yanmei et al. Integrated metatratranscriptomic and metagenomic analyses of stratified microbial assemblages in the open ocean, The ISME Journal (2011) 5, 999-1013 (Supplemental Materials).

* cited by examiner

Primary Examiner — Aaron A Priest
Assistant Examiner — Tian Yu
(74) Attorney, Agent, or Firm — Morgan, Lewis & Bockius LLP

(57) ABSTRACT

Provided are methods and systems for metagenomic analysis. Methods involve generating libraries and databases of taxonomic signatures informative of taxonomic information in a heterogeneous microbial sample. Methods also include identification of microorganisms and biochemical activities in the sample, including identification at a plurality of taxonomic levels.

33 Claims, 13 Drawing Sheets

| Organism | Actual Abundance | mOTUs qPCR Abundance Comparator | GOTTCHA Sample #237 | GOTTCHA Sample #232 | ViOmega Sample #237 | ViOmega Sample #232 |
|---|---|---|---|---|---|---|
| Bacillus subtilis | 13.50% | 11.86% | 6.18% | 4.58% | 5.71% | 4.90% |
| Clostridium botulinum | NA | 0.00% | 0.00% | 0.00% | *40.43% | *40.43% |
| Enterococcus faecalis | 11.40% | 14.84% | 7.83% | 5.40% | 6.87% | 7.54% |
| Escherichia coli | 11.60% | 9.17% | 8.97% | 5.81% | 7.30% | 5.48% |
| Lactobacillus buchneri | NA | 0.00% | *11.81% | *18.30% | 0.00% | 0.00% |
| Lactobacillus fermentum | 12.00% | 22.39% | 27.85% | 29.15% | 17.30% | 18.19% |
| Lactobacillus johnsonii | NA | 0.00% | *12.34% | *18.18% | 0.00% | 0.00% |
| Listeria monocytogenes | 12.50% | 15.01% | 5.84% | 4.10% | 9.40% | 5.80% |
| Pseudomonas aeruginosa | 12.10% | 5.88% | 6.77% | 4.86% | 6.39% | 5.90% |
| Salmonella enterica | 10.20% | 10.41% | 6.54% | 4.86% | 6.61% | 5.54% |
| Staphylococcus aureus | 13.00% | 10.43% | 6.37% | 4.77% | †0.00% | 6.22% |

\* False positive results are shown in bold green text (box)
† False negative results are shown in bold red text (box)

FIG. 8

SYSTEMS AND METHODS FOR METAGENOMIC ANALYSIS

REFERENCE TO RELATED APPLICATIONS

This application is a U.S. National Phase Application of PCT International Application PCT/US18/20539, filed Mar. 1, 2018, which claims the benefit of U.S. Provisional Application No. 62/465,747, filed Mar. 1, 2017, which applications are hereby incorporated by reference in their entirety.

STATEMENT AS TO FEDERALLY SPONSORED RESEARCH

This invention was made with government support under contract No. DE-AC52-06NA25396 between the United States Department of Energy and Los Alamos National Security, LLC for the operation of Los Alamos National Laboratory. The government has certain rights in the invention.

THE NAMES OF PARTIES TO A JOINT RESEARCH AGREEMENT

Certain inventions disclosed herein were made by one or more parties to a joint research agreement. The parties to the joint research agreement are Los Alamos National Security, LLC and BlueDot, LLC.

FIELD

The present disclosure relates in some aspects to computer systems, methods, and databases for analyzing metagenomics sequencing data. Provided in some embodiments are systems and methods that improve upon the performance of analyzing such data. The data can include sequencing data obtained from high-throughput or next-generation sequencing machines. Such data can be generated from samples obtained from a variety of sources, including subjects or the environment.

BACKGROUND

Microbial communities are not only found in nearly every environment from soils to oceans, to our bodies, but they also play an active role in maintaining the health and stability of these systems. Monitoring these communities enables a more complete understanding of how these environmental and health systems work, which ultimately will lead to interventions or treatments that will influence the state of these systems. Use of next generation sequencing (NGS) is becoming a common practice way to monitor these microbial systems. However, methods to accurately identify the specific taxonomic classification of the organisms contained in a microbial sample, as well as their relative abundance, in a reliable and time efficient manner, have remained a challenge.

SUMMARY

Provided herein are systems and methods for analyzing metagenomic samples, in particular metagenomic samples from a microbiome. After sample collection, the nucleic acid sequencing methods can be performed by computer. The methods involve, in some embodiments, generating a curated database of metagenomic information, identifying within the database sequence signatures for microorganisms at a plurality of different taxonomic levels and analyzing metagenomic transcriptome data to determine identity and/or quantity of microorganisms in the sample at each of the taxonomic levels.

In the curated metagenomic database, genome sequences for bacteriophages, plasmids and others for sequences can be removed from the genomes of each organism. Removal of these sequences serves to improve the performance of the systems and methods described herein by removing irrelevant data, thereby reducing the resources needed to process the metagenomic sample. Furthermore, duplicate genomes of the same microorganism can be limited (e.g. reduced or eliminated) from the database so that each microorganism is represented once in the database. This further increases the performance of the systems and methods by reducing or eliminating the need to check a single sequence against multiple copies of a genome or a taxonomic signature.

A library of taxonomic signatures contains, at each of a plurality of different taxonomic levels, nucleotide sequences specific for microorganisms at that taxonomic level. For example, at the genus level, signatures can be included that identify a microorganism as belonging to genus *Clostridium* or genus *Bacillus*. At the phylum level, signatures can be included that identify a microorganism as belonging to phylum Firmicutes. This Firmicutes signature would identify both *Clostridium* and *Bacillus*, but would not identify *E. coli*, which belongs to phylum Proteobacteria.

Some of the libraries or databases of sequence signatures can include sequences from open reading frames. Some of the libraries or databases exclude sequence signatures that are not encoded by open reading frames. These databases can increase performance by focusing on the information most informative for certain applications. For example, transcriptome analysis can be improved using sequence signature databases that are generated from the open reading frames of a plurality of genomes.

Analysis of the sample containing metagenomic information can involve both identifying microorganisms in the sample as well as quantifying them. This method can involve preparing a transcriptome library from the sample and mapping paired-end reads to the library of taxonomic signatures. Using various stringency criteria microorganisms at any taxonomic level can be called as present. In certain embodiments, criteria can involve mapping transcripts of sequences to genomic sequences that flank sequences in the library of taxonomic signatures, but that have been removed as representing sequence that is not specific to that taxonomic level. The methods can include the use of paired-end reads, in which the entire paired-end read is analyzed for sequence signatures informative of taxonomic information. In such cases, the best or most informative sequence signature detected in a paired-end read can be used to classify the entire read.

Taxonomic quantification can involve mapping transcriptome sequences to an open reading frame library, determining normalized gene expression for the organism and using relative normalized gene expression as an indication of quantity and/or activity of a microorganism.

One software embodiment of the methods described herein is referred to as ViOmega™.

BRIEF DESCRIPTION OF THE DRAWINGS

FIG. 8 shows tabular results obtained from an analysis of a commercially available microbial community standard sample (ZymoBIOMICS from Zymo Research), in which the results shown indicate which samples were identified according to embodiments of the present disclosure and their relative abundance and comparing to results obtained using the GOTTCHA and mOTUs metagenomics profiling tools.

DETAILED DESCRIPTION

Figure 1:
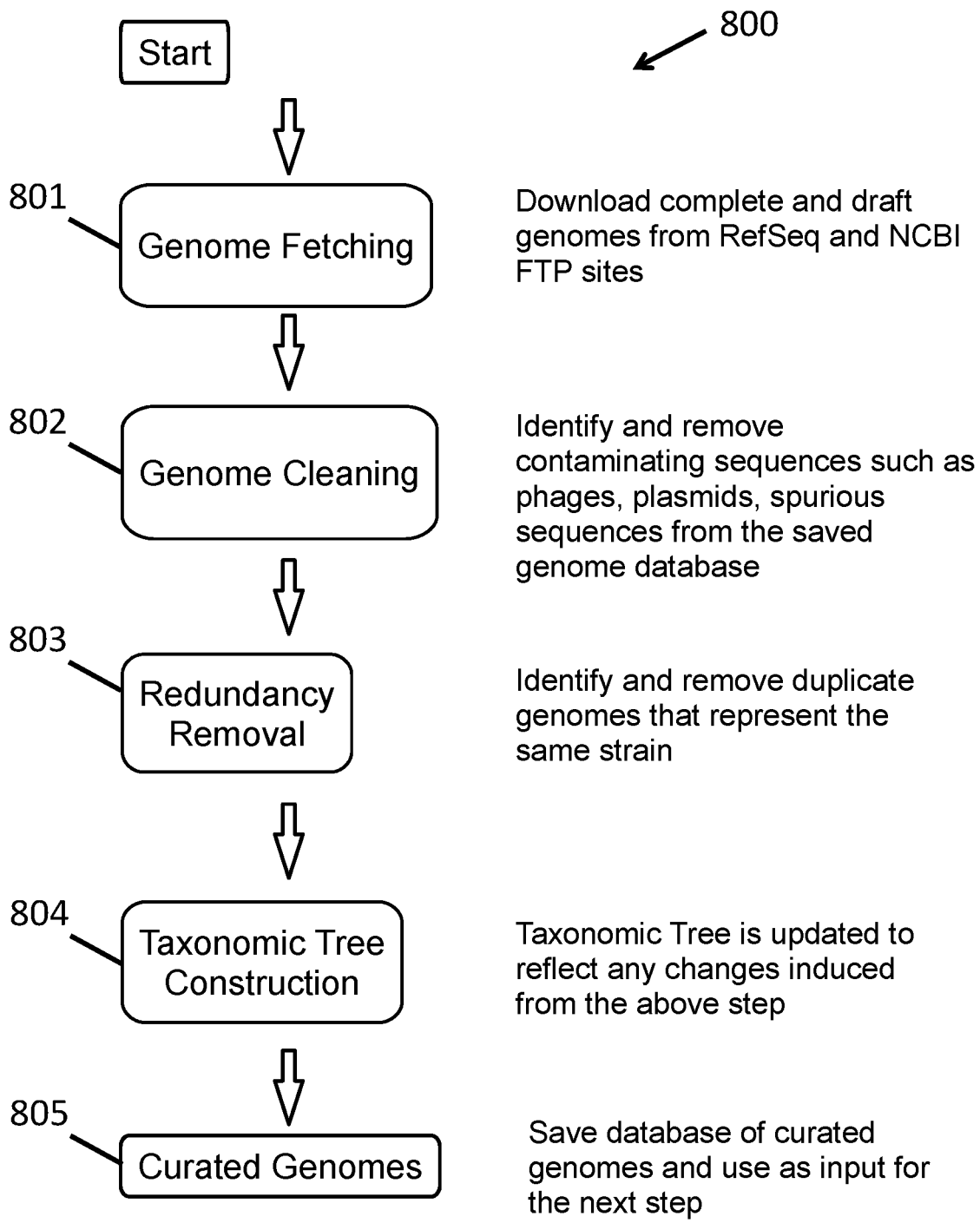
FIG. 1 shows a method of genomic database selection and curation.

Provided herein are systems, methods, databases, and libraries useful in classifying or identifying nucleic acid sequences present in a sample. The nucleic acid sequences can be used to classify or identify the organisms from which they arose. Such identification can include the identification of the organism as belonging to a category of organisms. Such a category can include a variety of taxa, including strain or sub-species, species, genus, family, order, class, phylum, kingdom or domain. Such a category can also include a biochemical activity. The systems have several advantages. For example, the systems are optimized to detect and store information that is useful in identifying a sequence as belonging to an organism at a specific taxon. Sequences that are not informative can be discarded. As a result, the systems described herein can run faster, require less storage and memory, and utilize less processor time than other methods—all while retaining the same or better accuracy and specificity in identifying the microbes in a metagenomic sample.

Some of the methods described herein identify a microbe or a biochemical activity in the sample using sequences derived from RNA in a sample. RNA can have several advantages in some circumstances. As an exemplary advantage, RNA can provide an indication of the composition of the microbes present in a sample. In another exemplary advantage, RNA can be informative of the biochemical activity of a sample. For example, genomic DNA contains sequences to pathways that may or may not be active in some circumstances. In contrast, RNA can provide a record of the transcripts being produced by microbes in the sample, which can be informative of the biochemical activity of those microbes in the sample. Furthermore, RNA can be used to quantify particular biochemical activities in a sample. This can include the amount of an enzyme related to a particular pathway or process. For example, RNA transcript quantification of genes related to butyrate production can be informative of the amount of butyrate being produced by a sample and the organisms contributing to that production.

The signatures described herein can be used to identify or classify organisms by a variety of different systems. Such systems can include classical or modem taxonomic classification systems.

As used herein, the term "taxon" (plural "taxa") is a group of one or more populations of an organism or organisms seen by taxonomists to form a unit. A taxon is usually known by a particular name and given a particular ranking. For example, species are often designated using binomial nomenclature comprising a combination of a generic name for the genus and a specific name for the species. Likewise, subspecies are often designated using trinomial nomenclature comprising a generic name, a specific name, and a subspecific name. The taxonomic name for an organism at the taxonomic rank of genus is the generic name, the taxonomic name for an organism at the taxonomic rank of species is the specific name, and the taxonomic name for an organism at the taxonomic rank of subspecies is the subspecific name, when appropriate.

As used herein, the term "taxonomic rank" is the relative level of a group of organisms (a taxon) in a taxonomic hierarchy. Examples of taxonomic ranks are species, genus, family, order, class, phylum, kingdom, and domain. Other examples of taxonomic ranks include microspecies, strain, subspecies, and quasispecies. As used herein, the term "taxonomic level" refers to a rank in a taxonomic hierarchy of organisms such as, strain, species, genus, family, order, class, phylum, and kingdom. In some embodiments, each taxonomic level includes a plurality of "taxonomic members", that is, the different members belonging to particular taxonomic level. Some taxonomic levels only include a single member. Taxonomic rank and taxonomic level are used interchangeably.

As used herein, the term "species" is intended to encompass both morphological and molecular methods of categorization. Species can be defined by genetic similarity. Sequence signatures can be used to define or distinguish between species. In some embodiments, a cladistic species is an evolutionarily divergent lineage and is the smallest group of populations that can be distinguished by a unique set of morphological or genetic traits.

I. METHODS OF CREATING CURATED METAGENOMIC DATABASES

In one aspect provided herein is a curated metagenomic database. A first step in the generation of the database is to access a collection of sequenced non-human, microorganism genomes deposited in a genomic database, such as NCBI (draft and/or finished genomes), and to save these into a new database to create a collection of genomes. The taxonomic levels and phylogenetic relations are also saved and used as input. These reported genome sequences are then cleaned of sequencing and assembly artifacts introduced from foreign sources (e.g., contamination of source DNA of genome by bacteriophages, plasmids or other organisms). Genomes are then checked for redundancy, and all duplicates are removed so no distinct genome is represented more than once. A duplicate genome may be considered to be one with at least 95%, at least 97%, at least 98% or at least 99% sequence identity with another genome. Each unique genome signature in the collection is then taxonomically labeled according to the sequences that characterize each distinct taxonomic level. Each genome may be labeled with a plurality of different taxonomic level labels ranging from phylum through strain, and any/all taxonomic levels in between, according to the taxonomy level data saved from the original database source.

In one aspect provided herein is a method of developing a library of taxonomic signatures. Taxonomic signatures can be specific to different taxonomic levels. Taxonomic signatures comprise nucleotide sequences common to members of that taxon at that level and unique with respect to other taxa at that level. Sequences that are common across all members at that level can be identified and labeled as the member's unique signature profile (signature sequence). Sequences that are unique to at least one member of a taxonomic level can also be identified and labeled as a signature sequence for that taxonomic level. For example, a sequence signature found in three of the five members of a genus can be informative of the presence of a member of that genus. Alignment of sequence reads (e.g., from a sample) to this unique signature profile is what identifies the presence of this member in a sample. A way these unique reference genome signatures are created at a specific taxon level can involve the following steps.

Genomes representing a taxon (or taxonomic member) at a specific taxonomic level are grouped. Thus, a taxon is composed of the entities representing a specific strain, species, genus, etc. Genomes can include the full set of genome sequence information per taxonomic ranking. The genomic information for a particular taxon used in the methods described herein can include the genomes or sequence information for more than one member of the taxon. So, for example, genome for a species can include the full set of strain genome sequences for that species.

For each taxonomic member, a distinct set of k-mers can be determined from the member genomes. A k-mer is any ordered set of k nucleotides regardless of position in the genome, and specifically a k-mer of length 24 (a 24-mer) and a k-mer of length 30 (a 30-mer) were empirically determined to be useful. In some aspects, the k-mer has a length of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or any integer between 5 and 100. K-mers can be generated by scanning the genomes with a window that is the length of the k-mer.

K-mers can be compared across different taxonomic members (e.g., members of a taxon) at the same taxonomic level. Different windowing methods are contemplated. In some methods, a genome can be divided into non-overlapping k-mers. Non-overlapping k-mers can include creating a k-mer at a first location in the genome and sliding the window any number of nucleotides that is equal to or greater than the total length of the k-mer along the sequence of the genome to create the next k-mer. The k-mers will contain non-overlapping sequence because the window length is equal to or greater than the k-mer length. In other aspects, a genome can be divided into overlapping k-mers. Overlapping k-mers can include creating a k-mer at a first location in the genome and sliding the window any number of nucleotides that is less than the total length of the k-mer along the sequence of the genome to create the next k-mer. The k-mers will contain overlapping sequence because the window length is less than the k-mer length. The performance of the databases, systems, and methods described herein can be optimized for a particular use by adjusting k-mer length and windowing methods. In some aspects, using non-overlapping k-mers reduces the number of k-mers produced, analyzed, or stored because a single nucleotide is only represented by at most one k-mer window. Non-overlapping k-mers can also help simplify the assembly of k-mers into longer contigs when such contigs are used as sequence signatures. Increasing k-mer length also reduces the number of k-mers produced in both overlapping and non-overlapping windowing methods. Thus, subsequent sample analysis steps can utilize fewer computational resources used in some circumstances because fewer sample alignments need to be performed against the sequence signature database. Decreasing k-mer length can also reduce the computational resources used in some circumstances because each sample alignment performed by the analysis is compared to a shorted signature sequence.

In some aspects, k-mers that are present in more than one member of the same taxon are not informative of identifying the members of the taxon. K-mers that are present in more than one taxonomic member at the same taxonomic level can be removed from the genomes of those members. Alternatively, K-mers that are present in more than one taxonomic member at the same taxonomic level can be removed from the genomes of those members at the corresponding taxonomic level. The k-mers that remain after comparing k-mers across different taxonomic members and removing k-mers that are present in more than one taxonomic member can be used as sequence signatures informative of a taxonomic designation. Alternatively, as k-mers are removed from the genomes, the remaining sequences can be used as sequence signatures. Such sequence signatures may be longer than the k-mers used in the analysis. Alternatively or in addition, related and overlapping k-mers that are informative of a particular taxon can also be compiled into longer contigs. The contigs can be used as sequence signatures.

For example, if an analysis is comparing members of the genus Bacillus and a sequence is present in only *B. subtilis* but not other members of the genus, the sequence can be a sequence signature informative of *B. subtilis*. Likewise, if the sequence is present in *B. subtilis* and *B. licheniformis*, but not in other members of the family Bacillaceae, then the sequence can be a sequence signature informative of the presence of a member of the genus *Bacillus* in the sample.

In some embodiments, the sequence signature is unique to the particular taxon across all known genomes. The sequence signature may also be unique within a database suitable for a particular type of sample. Thus, if the presence of a particular taxon is not expected to be present in a particular sample, genomes from that taxon may be excluded when generating sequence signatures. As an example, a method of generating a database useful in analyzing a stool sample might exclude sequences from extremophiles that are only found in underwater hydrothermal vents.

Furthermore, k-mers that are found in a perspective prospective host genome, for example a human genome (e.g., GRCh37.p10) can be removed from the remaining genome sequence. This can be useful in reducing false positives when analyzing a sample if a sequence that exists in a microbe also exists in a host genome. The methods for removing sequences that are present in a microbe and a host can be the same as those described above. In some aspects, a host genome can be added to the collection of genomes analyzed above and analyzed concurrently with the methods of generating a database. In some aspects, a database can be generated for a plurality of microbes using the methods above first and the database can be further compared to a host genome to remove common sequences.

In some aspects, the performance or accuracy of the databases can be improved by removing sequences that are abundant in a sample but that can be largely uninformative of sample composition. For example, ribosomal RNA, mtDNA, tRNA and others can be found in very high abundance in many metatranscriptomic sequence libraries, and can lead to false positives due to high homology or sequence correlation across different taxonomical members. These sequences (e.g. regions) thus can be filtered out from the profiles with greater stringency then the rest of the sequence. To do this a (k–n)-mer can be used. A (k–n)-mer can be a nucleotide sequences that is n nucleotides shorter than k, to filter out common sequences. For example, if k is 24, and n is 4, then all common 20-mers between taxonomic members are identified and removed. In some aspects, k can be 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some aspects, n can be 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49. Likewise, a k-mer can be used to filter out common sequences between a host and the microbial genomes contained in a database.

The accuracy and performance of the database can be further improved by increasing the size thresholds for sequence signatures. Thus, sequence signatures that are lower than a threshold size can also be removed from the database. Removal of these smaller sequences can further reduce the size of the database as fewer sequences meet the threshold. Removal of these smaller sequences can reduce the number of sequences against which a sequence read from a sample must be compared, thereby increasing the performance of the database or reducing the computing resources necessary to perform the methods. Removal of these sequences can also increase the accuracy of a database's ability to identify particular taxa as longer sequences increase the length of sequence over which homology between a sequence read and a sequence signature is compared. Sequences in the genomes fewer than 30 nucleotides long can be removed, although other lengths are also contemplated herein. For example, sequences in the genomes fewer than 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 can be removed. Removing such sequences can improve the performance of the database by reducing the number of total sequences in the database, reducing the number of sequences that are less informative of taxonomic information from the database relative to longer sequences, etc. In some aspects, removing such sequences can reduce the size of the database, the amount of memory required to run the sequence signature generation analysis, the number of CPU cycles required to run the sequence signature generation analysis, the amount of storage required to store the database, the amount of time needed to compare sample sequences to the database, the number of alignments that must be performed to identify sequence signatures in a sample, the amount of memory required to run the sequence signature sample analysis, the number of CPU cycles required to run the sequence signature sample analysis, etc.

So, for example, at the phylum taxonomic level, all genomes would be grouped by phylum. K-mers by phylum are then identified, and any k-mers found in any member of more than one phylum would be removed from all genomes. What remains is a taxonomic signature of each phylum member.

Remaining sequences represent sequences unique to taxonomic members at the taxonomic level. The amount of genome lost (e.g., removed as uninformative) depends on the taxonomic level desired. Some very small genome segments differentiate species. One method for determining the minimum length of a sequence signature includes varying the minimum length of sequence signatures and testing those signatures on synthetic genome or RNA transcript datasets with known quantities of sequences from known genomes. For example, the length of a genome segment or sequence signature can be at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides long. A minimum 30-nucleotide length was empirically determined to be useful, although other lengths are also contemplated.

This process can be repeated at a one or more different taxonomic levels.

In one embodiment of the present invention, optimization of signature database creation utilizes machine-learning methods for training and validating the signature database. Sequence signatures can also be validated against synthetic sequence mixtures with known compositions that include the genomes of taxa not included in the database. The sequence mixtures can also contain sequences generated at random and sequences from a variety of host genomes, such as a human genome. In another embodiment, machine learning methods are used to empirically derive thresholds for establishing sensitivity and/or specificity during metagenomic profiling.

II. OPEN READING FRAME LIBRARIES

In another aspect provided herein is a method performed by computer for generating an open reading frame library. One step of the method involves providing a curated metagenomic database comprising genomes of different microorganisms, such as that described above. The genomes can be complete or partial genomes. The genomes are then scanned to identify open reading frames. Tools to identify open reading frames include, for example, ORF Finder or MetaGene ("MetaGene: prokaryotic gene finding from environmental genome shotgun sequence", H. Noguchi, J. Park and T. Takagi Nucleic Acids Research (2006) 34(19):5623-5630). A plurality of open reading frames identified are then mapped to an annotated catalog of metagenomic open reading frames. Such a catalog can be found at, for example, Li et al., MetaHIT Consortium, "An integrated catalog of reference genes in the human gut microbiome," Nat Biotechnol. 2014 August; 32(8):834-41. doi: 10.1038/nbt.2942. PubMed PMID: 24997786. In some embodiments, no more than 10%, no more than 5%, no more than 2% or no more than 1%, of the sequences in an open reading frame library represent sequences other than open reading frames.

The open reading frame database can be used as described above or can be further processed or analyzed. In one example, the sequences in the database can also be stratified by taxonomic rank. In another example, sequence signatures can be identified within the open reading frame database by comparing the sequences of different genomes and identifying sequences informative of taxonomic information. Such methods include those described above for genomic databases.

Alternatively or in addition, the open reading frame database can be further processed or analyzed by identifying open reading frames that are associated with a particular biochemical activity or pathway. Such methods can include identifying the gene that encodes the open reading frame, the protein or functional RNA molecule encoded by the open reading frame, the function or activity of the protein or functional RNA molecule encoded by the open reading frame, or a product or metabolite produced by the protein or functional RNA molecule encoded by the open reading frame. Examples of biochemical activities include enzymes and pathways related to breaking down polysaccharides (including starches, fiber, oligosaccharides, lactose, sugar alcohols), mucus, and proteins. Other examples include production of acetic acid, propionic acid, butyric acid, biotin and folate. In yet other examples, the biochemical activity includes absorption of minerals, such as calcium, magnesium, and iron.

Open reading frame signature sequences, databases, and libraries can have several exemplary advantages over genomic sequence signature databases under some circumstances. Open reading frames represent a proportion of the total genome of a microorganism. Discarding the non-coding sequences in a genome can help to reduce the total number of sequences stored in the database. Alternatively or in addition, open reading frames can be particularly useful when analyzing a transcriptome of a heterogeneous sample, such as a sample comprising a plurality of different microorganisms. Discarding non-coding sequences can remove uninformative sequence information from the database when the database is used for this purpose. Likewise, open reading frame sequence signatures can be particularly helpful when analyzing the quantity or activity of a particular biochemical process present in a sample.

In some aspects, removing such sequences can reduce the size of the database, the amount of memory required to run the sequence signature generation analysis, the number of CPU cycles required to run the sequence signature generation analysis, the amount of storage required to store the database, the amount of time needed to compare sample sequences to the database, the number of alignments that must be performed to identify sequence signatures in a sample, the amount of memory required to run the sequence signature sample analysis, the number of CPU cycles required to run the sequence signature sample analysis, etc.

III. SAMPLE ANALYSIS

A. Sample Isolation

The databases, systems and methods described herein can be used to analyze the compositions of samples. In some aspects, the databases can be used to analyze the composition of a heterogeneous microbial sample. Various types of samples are contemplated herein. These include samples from a subject.

The samples analyzed by the methods and systems described herein comprise heterogeneous microbial populations. Microbial communities are often made up of mixed populations of organisms, including unknown species in unknown abundances.

In some aspects, the sample can be from a species of a mammal, a species of a rodent, a species of a mouse, a species of a rat, a species of a dog, a species of a cat, a species of a hamster, a species of a monkey, a species of a pig, a species of a squirrel, a species a guinea pig, a species of a gerbil, a species of a bird, a species of a hydra, a species of a rabbit, a species of a fish, a species of a frog, a species of a cow, a species of a lamb, a species of a chicken, a species of *Drosophila,* a species of *Xenopus,* a species of horse, and a human.

A sample used in a methods described herein may be, for example, earwax, sweat, breast milk, hair, blood, bile, cerebrospinal fluid, lymphatic fluid, semen, vaginal discharge, menstrual fluid, feces, sputum, urine, saliva, secretions from open wounds, secretions from the eye, skin tissue (e.g., a skin biopsy), subcutaneous tissue, muscle tissue, adipose tissue, and a combination thereof.

Furthermore, a sample may be obtained from, for example, the gut, the vagina, the penis, a testicle, the cervix, the respiratory system, the ear, the skin, the rectum, the kidney, the liver, the spleen, the lung, the pancreas, the small intestine, the gallbladder, the lymph nodes, the colon, a nasal passage, the central nervous system, an oral cavity, a sinus, a nostril, the urogenital tract, an udder, an auditory canal, a breast, an open wound, the eye, fat, muscle, and combinations thereof.

In some aspects, the sample can be an environmental sample or an agricultural sample. Examples include samples from soil, plant/fruit samples taken during a planting or harvesting, must, sampling of wine during alcoholic fermentation (beginning, middle and end, or depending on parameters such as alcoholic graduation, amount of sugar, density), sampling during malolactic fermentation (beginning, middle and end, or depending on amount of malic and acetic acid), barrel (beginning, middle and end, or months) and bottling. Other examples include samples from sites containing contaminants, including those associated with petroleum extraction and refining, chemical manufacturing, pesticide use, etc.

In some aspects, the sample can be one used to detect pathogenic microbes or microbes used in a bioterrorism attack. Such a sample includes analysis of microbes collected in an air filter or by sampling a surface. In some embodiments, the sample is a forensics sample.

Polynucleotides can be extracted directly from the sample, or cells in the sample can first be lysed to release their polynucleotides. In one method, lysing cells comprises bead beating (e.g., with zirconium beads). In another method, ultrasonic lysis is used. Such a step may not be necessary for isolating cell-free nucleic acids.

Nucleic acids can be isolated from the sample by any means known in the art. Polynucleotides can be isolated from a sample by contacting the sample with a solid support comprising moieties that bind nucleic acids, e.g., a silica surface. For example, the solid support can be a column comprising silica or can comprise paramagnetic silica beads. After capturing nucleic acids in a sample, the beads can be immobilized with a magnet and impurities removed. In another method, nucleic acids can be isolated using cellulose or polyethylene glycol.

If the target polynucleotide is RNA, the sample can be exposed to an agent that degrades DNA, for example, a DNase. Commercially available DNase preparations include, for example, DNase I (Sigma-Aldrich), Turbo DNA-free (ThermoFisher) or RNase-Free DNase (Qiagen). Also, a Qiagen RNeasy kit can be used to purify RNA.

Alternatively or in addition, a sample comprising DNA and RNA can be exposed to a low pH, for example, pH below pH 5, below pH 4 or below pH 3. At such pH, DNA is more subject to degradation than RNA.

If the target polynucleotide is RNA, the sample can be reverse transcribed into DNA. Reverse transcription generally takes place after a sample has been depleted of DNA.

In some aspects, a sample can be depleted of nucleic acids and nucleic acid species that are abundant relative to other nucleic acids in the sample. Some of the abundant nucleic acids may not be target nucleic acids (e.g., they may not encode sequence signatures or may not be informative of desired taxonomic information). The presence of these abundant nucleic acids can reduce the sensitivity of some of the methods described herein. This can be true, for example, if target or informative nucleic acids are rare relative to the abundant nucleic acids. Therefore, it can be advantageous to enrich a sample for target sequences by removing non-informative abundant sequences. Examples of sequences that can be removed include microbial ribosomal RNA, including 16S rRNA, 5S rRNA, and 23S rRNA. Other examples of sequences that can be removed include host RNA. Examples include host rRNA, such as 18S rRNA, 5S rRNA, and 28S rRNA.

Methods of enriching nucleic acid samples include the use of oligonucleotide probes. Such probes can be used for either positive selection or negative selection. Such methods often reduce the amount of non-target nucleotides.

If the target polynucleotide is DNA, then DNA can be isolated with silica, cellulose, or other types of surfaces, e.g., Ampure SPRI beads. Kits for such procedures are commercially available from, e.g., Promega (Madison, Wis.) or Qiagen (Venlo, Netherlands).

The isolated nucleic acids are generally sequenced for subsequent analysis. The methods described herein generally employ high throughput sequencing methods. As used herein, the term "high throughput sequencing" refers to the simultaneous or near simultaneous sequencing of thousands of nucleic acid molecules. High throughput sequencing is sometimes referred to as "next generation sequencing" or "massively parallel sequencing." Platforms for high throughput sequencing include, without limitation, massively parallel signature sequencing (MPSS), Polony sequencing, 454 pyrosequencing, Illumina (Solexa) sequencing, SOLiD sequencing, Ion Torrent semiconductor sequencing, DNA nanoball sequencing, Heliscope single molecule sequencing, single molecule real time (SMRT) sequencing (PacBio), and nanopore DNA sequencing (e.g., Oxford Nanopore).

B. Transcriptome Sequence Preprocessing

Also provided herein are methods of analyzing RNA transcripts in a heterogeneous microbial sample. The RNA transcripts can be part of a transcriptome for a cell or cells in the heterogeneous microbial sample. The methods generally include isolating and sequencing the RNA found in a sample as described above.

The sequences obtained from these methods can be preprocessed prior to analysis. If the methods include sequencing a transcriptome, the transcriptome can be preprocessed prior to analysis. In one method, sequence reads for which there is paired-end sequence data are selected. Alternatively or in addition, sequence reads that align to a reference genome of the host are removed from the collection. This produces a set of host-free transcriptome sequences. Alternatively or in addition, sequence reads that encode non-target nucleotides can be removed prior to analysis. As described above, non-target nucleotides include those that are over-represented in a sample or non-informative of taxonomic information. Removing sequence reads that encode such non-target nucleotides can improve performance of the systems, methods, and databases described herein by limiting the sequence signature database to open reading frames can the size of the database, the amount of memory required to run the sequence signature generation analysis, the number of CPU cycles required to run the sequence signature generation analysis, the amount of storage required to store the database, the amount of time needed to compare sample sequences to the database, the number of alignments that must be performed to identify sequence signatures in a sample, the amount of memory required to run the sequence signature sample analysis, the number of CPU cycles required to run the sequence signature sample analysis, etc.

C. Taxonomic Identification

1. Sequence Alignment

To determine the identity of one or more organisms present in a sample at a specific taxonomic level, paired-end (or optionally single) reads from that sample are aligned to the library of taxonomic signatures as described herein at that specific taxonomic level. The reads can be genomic or transcriptomic sequencing reads. Sequences can be aligned using, for example, the BWA aligner with the mem algorithm. (Li H. (2013) "Aligning sequence reads, clone sequences and assembly contigs with BWA-," arXiv: 1303.3997v1 [q-bio.GN].) BWA is often run with a minimal seed alignment length of 30 nt, but other BWA parameters such as the mis-match penalty can be modulated, as can downstream filters. Global thresholds for sensitivity and specificity can be tuned at this level by modulating the BWA parameters during model training after taxonomic signature generation on test data sets of known composition. These values can then be applied during the identification step. The best unique alignment of a read or read pair to a unique genome signature at a specific taxonomic level can be used to identify that taxonomic member as being present. Some organisms will be identified to the strain taxonomic level while others may only be identified to the genus level (or higher) depending on the nature of distinct sequences available in the database to make an accurate determination.

In some aspects, the alignment uses single or paired-end reads. In some aspects, alignment uses sequence information from both a forward read and a reverse read of a paired-end read. The sequencing reads can be partitioned or non-partitioned reads. Partitioned reads include partitioning the reads into a series of overlapping or non-overlapping segments, such as K-mers. K-mers can have a predetermined length. For example, the length can be 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 60, 70, 80, 90, 100, 125, 150 or more nucleotides long. K-mers can then be compared to sequence signatures in the database using the methods described herein.

Non-partitioned reads can also be compared to sequence signatures using the methods described herein. In some aspects, the non-partitioned read is a complete read from a sequences. In some aspects, the non-partitioned read is processed such that only a portion of the read corresponding to the nucleotide from the sample is compared to the sequence signatures. This can include processing the reads such that primer binding sites, barcodes, or adapter sequences are not included in the sequence signature analysis. The disclosure also contemplates using a portion of a read that passes quality control criteria, such as a confidence score. In some aspects, one or both ends of a paired-end read can be used. In some aspects, a single end read or an end of a paired-end read can be 20, 21, 22, 23, 24, 25, 26, 27, 28, 29, 30, 31, 32, 33, 34, 35, 36, 37, 38, 39, 40, 45, 50, 60, 70, 80, 90, 100, 125, 150 or more nucleotides long. Using paired-end reads (e.g., sequence information from both the forward and reverse reads of a paired end read) can effectively double the amount of read length available for analysis.

The non-partitioned reads can be aligned to signature sequences using the methods above. Using non-partitioned reads can offer several advantages. First, contiguity information for each paired-end read can be maintained. Thus, both ends of a paired-end read can be identified as arising from the same nucleic acid molecule of origin. Thus, it can be inferred that both ends originated from the same cell, and further it can be inferred that both ends originated from the same organism. In general, where a non-partitioned read is determined to contain more than one signature sequence, a signature sequence that is most informative of the taxonomic information of the entire read is selected to represent the entire paired-end read. For example, if a first portion of a paired-end read contains a sequence signature that is informative of a subspecies, a second portion contains a sequence signature that is informative of a species, and a third section is informative of a genus, the entire sequence read, and thus the molecule the sequence read originated from, can be identified by the subspecies. Both ends are identified as originating from the subspecies using the most informative sequence signature detected. This is because both reads of the read pair are present on the same molecule and originated from the same cell even if the sequence signatures detected in each read vary in specificity.

The non-partitioned reads can also be advantageous over partitioned reads because of the increase in sequence length aligned against the sequence signatures. The use of non-partitioned reads can allow for the detection of sequence signatures containing differences that are more than one k-mer nucleotides apart at the same time, whereas the use of partitioned reads requires the unique signature to be present in a smaller sequence. For example, while sequence signatures for a pair of k-mers may only be able to identify the k-mers at the genus or family level, sequence signatures analyzing a longer non-partitioned read comprising the two k-mers may be able to identify the sequence as arising at the subspecies level. Thus, non-partitioned reads can be analyzed with increasing levels of specificity and accuracy. This increase in specificity and accuracy offers several advantages. One advantage includes the fact that identifying a sequence as belonging to a more specific taxonomic rank decreases the uncertainty of the composition of the species present in the heterogeneous microbial sample. A sequence signature that can only identify a read as originating from a particular genus or family leaves more uncertainty that a read that can be identified at the species level. For example, it may be unclear if a read identified at the genus level arises from a known species or an unknown species, from a pathogenic species or a non-pathogenic species, etc.

Another advantage of the use of non-partitioned reads includes the ability to retain contiguity information for an entire read during the analysis. Retaining contiguity can allow the entire read, including a paired-end read, to be identified as arising from the most specific toxon identified using taxonomic sequence signatures. In contrast, methods using k-mers often do not retain contiguity information. As a result, two k-mers partitioned from the same read may be independently identified by different sequence signatures at different taxonomic ranks. It can be difficult to determine if these sequences arose from the same organism or different organism. As a result, the results can be more ambiguous and quantification can be less accurate as a k-mers arising from single molecule may be assigned to more than one taxon.

Using non-partitioned reads can also offer performance advantages over k-mers. Methods using non-partitioned reads may require fewer alignments to complete the analysis. This advantage can arise for several reasons. For example, a single non-partitioned read can be the length of several K-mers. By not dividing the read into k-mers, fewer alignments need to be performed. As another example, an entire non-partitioned read can be labeled by the most informative sequence signature. Thus, once a read is identified at a lower taxonomic rank, the read may not need to be checked against signatures for higher order taxonomic ranks. Furthermore, weaker, less informative sequence signatures mapping to that read can be discarded. In contrast, each k-mer needs to be assessed independently even if other k-mers arising from the same read have already been identified. In yet another example, each read is generally stored in a database or output file. A non-partitioned read can be stored only once, along with the identifying information and results. In contrast, each partitioned read may need to be independently analyzed, identified, and stored. The use of non-partitioned reads, therefore, can decrease the resources, such as computational resources, needed to complete the analysis.

In some aspects, a microorganism or a taxon is identified as being present in the sample if 1, 2, 3, 4, 5, 6, 7, 8, 9, 10, 15, 20, 25, 30, 35, 40, 45, 50, 60, 70, 80, 90, 100 or more sequence signatures corresponding to the taxon are detected in the sample. In some aspects, a microorganism or a taxon is identified as being present in the sample if 1, 2, 3, 4, 5, 6, 7, 8, 9, 10, 15, 20, 25, 30, 35, 40, 45, 50, 60, 70, 80, 90, 100 or more sequence reads are detected for a sequence signature in the sample. In some aspects, a read is determined to match a sequence signature if the read is 90%, 95%, 96%, 97%, 98%, 99%, 99.5%, 99.9% or 100% identical to at least a portion of the sequence signature or the entire sequence signature. In some aspects, a read is determined to match a sequence signature if the sequence signature is 90%, 95%, 96%, 97%, 98%, 99%, 99.5%, 99.9% or 100% identical to at least a portion of the read or the entire read. In a preferred embodiment, calling or identifying a microorganism as being present at one or more taxonomic levels requires at least 1, 2, 3, 4, 5, 6, 7, 8, 9, 10, 11, 12 13, 14, 15, 20, 25, 30, 35, 40, 50, 60, 70, 80, 90, or 100 reads of at least 10, 15, 20, 25, 30, 40, 50, 60, 70, 80, 90, 100, 110, 120, 130, 140, or 150 nucleotides and a mismatch rate no greater than 2% when aligned against the curated database/library of unique genome signatures.

Alternatively or in addition, the methods, systems and databases herein can be used to identify a biochemical activity present in the sample. In some embodiments, the methods include determining the presence of an organism belonging to a taxon, as described above, generating or using a database comprising a genome of the organism or taxon as described above, and aligning sequencing reads to the database comprising open reading frame information. Such information can be used to identify sequences that are associated with a particular biochemical activity or pathway, including biochemical activities associated with the taxon. Some of such methods can include identifying taxonomic information for a sequence. Some of such methods do not include identifying taxonomic information for the sequence, but instead may identify the biochemical activity, pathway, protein, functional RNA, product, or metabolite associated with a particular sequence read or sequence signature. The sequence reads can include those that contain a taxonomic signature or sequence information obtained from a sample regardless of the presence of a sequence signature. For example, the methods can include mapping up to and including all of the sequence reads obtained from a sample.

2. Use of Flanking Sequences

In another embodiment, transcriptome sequences that align to one portion of the unique genome signature database/library but do not align to sequences flanking the first portion in that alignment are eliminated.

In one version of this embodiment, identification of organisms on a particular taxonomic member at a taxonomic level can be determined by making use of sequences that flank sequences in the taxonomic signature. That is, the method can make use of sequences of the genome removed from the genome in the generation of the taxonomic signature. In this method transcriptome sequences are often first aligned to the taxonomic signature sequences. Then, portions of the aligned transcriptome sequences that do not, themselves, align with the signature sequences can be compared to the sequences that flank the signature sequences. If there is insufficient homology between these flanking sequences, the entire sequence read can be removed from the alignment protocol. The minimum level of homology required for a sequence to remain in alignment can be, for example, at least 90%, at least 95%, at least 98%, at least 99% or 100%.

D. Microorganism Quantification

The methods, systems, and databases described herein can also be used to quantify a characteristic in a heterogeneous sample. In one aspect, provided herein are methods for quantifying microorganisms in a sample. Alternatively or in addition, provided herein are methods for quantifying a particular biochemical activity associated with a heterogeneous microbial sample or a microorganism contained therein. Transcriptome sequences from the sample can be mapped to the ORF library described above. In some aspects, ORF library can be used to infer taxonomic information about the organisms present in the sample. Alternatively or in addition, sequences that map to the library can be annotated to indicate information such as gene identity and gene function. The methods can include determining the presence of an organism belonging to a taxon, as described above, generating or using a database comprising a genome of the organism or taxon as described above, and aligning sequencing reads to the database comprising open reading frame information. The sequence reads can include those that contain a taxonomic signature or sequence information obtained from a sample regardless of the presence of a sequence signature. For example, the methods can include mapping up to and including all of the sequence reads obtained from a sample.

Quantification of abundance can be done by computer by summing up the non-overlapping length of profiles found for a taxonomic member (Linear Length or L), then determining the read coverage across that length (Linear Depth of Coverage or DOC). In some aspects, the non-overlapping length is or comprises a sequence signature informative of taxonomic information.

Normalizing over the sum of all DOCs for a specific taxonomic level allows one to arrive at the relative abundance (RA) of that taxonomic member. In one embodiment, normalization comprises: determining the number of base pairs contained in a particular ORF, determining an average depth of coverage for the entire length of the ORF using the number nucleotides contained in sequence reads corresponding to the ORF and the length of the ORF, and determining the proportion of all sequence reads that correspond to the ORF.

Normalization can comprise determining an average depth of coverage for ORFs that belong to organisms or taxa that are identified in the sample from the sequencing data, summing the averages to generate a total depth of coverage, and dividing the depth of coverage for an ORF of interest by the total depth of coverage. Such a method can be used to determine a relative amount or proportion of sequence reads for the target ORF in the sequencing data. Such methods can also account for the relative differences in lengths of ORFs, allowing for more direct comparisons, because the methods can use the depth of coverage for an ORF rather than the total number of bases read. Thus, a number of base reads in a 1,000 bp ORF would have half the total depth of coverage compared to the same number of base reads in a 500 bp ORF. The relative amount or proportion of the ORF in the sample can be used to infer the relative activity of the target ORF.

The measure of gene expression at each taxonomic level can be calculated based on the Reads Per Kilobase (RPK) of transcript per Million mapped reads. Additional filters can be applied at this step on read count, L, DOC, or RA with thresholds determined during the model training step. Note this relative abundance will be for the DNA or RNA fraction of that taxonomic member in the sample at time of library prep. If the source was RNA, then the relative abundance calculated can correspond to the relative activity of that organism in the sample (e.g., gene expression levels). Alternatively or in addition, if the source was RNA, then the relative abundance calculated for an ORF can correspond to the relative activity of that ORF, including the activity or pathway. If the source was DNA, one relates to relative abundance of that organism assuming a single genome copy per organism. The taxonomic relative activity can be quantified by finding the median or mode of non-zero Reads Per Kilobase (RPK) of transcript per Million mapped reads (RPKM values) and inversing scaling by the fraction of active genes.

The output of this process can be a report that indicates for a subject sample the taxa of microorganisms in the sample. If the taxonomic identity of the sample cannot be identified at a particular taxonomic level the report can indicate the intensity at the next highest taxonomic level. The report can also indicate quantitative information about the sample this can include, for example, the relative amounts of different microorganisms in the sample. It can also indicate relative activity of microorganisms in the sample based on relative gene expression. This can include, for example, types of genes that are either expressed in high amounts or alternatively, in low amounts. Alternatively or in addition, the report can indicate the identity and relative amounts of biochemical activities in the sample. The report can indicate changes as to biochemical activity in the sample over time, such as during a time course. The report can indicate differences between samples, including samples collected from the same source at different times. The source can be a subject, such as a human subject.

In some aspects, limiting the sequence signature database to open reading frames can reduce the size of the database, the amount of memory required to run the sequence signature generation analysis, the number of CPU cycles required to run the sequence signature generation analysis, the amount of storage required to store the database, the amount of time needed to compare sample sequences to the database, the number of alignments that must be performed to identify sequence signatures in a sample, the amount of memory required to run the sequence signature sample analysis, the number of CPU cycles required to run the sequence signature sample analysis, etc.

Reports can sometimes be output to paper, a screen, or a database. Reports can also be stored for later analysis or viewing. Reports can be sent to third parties, such as subjects, healthcare professionals, customers, collaborators, etc.

IV. SAMPLES

The methods described herein can be used to assess heterogeneous microbial populations. Typically, the heterogeneous microbial populations are assessed as a sample. Exemplary samples include samples from a subject, a plant, soil, a water source, an air filter, a surface, a container, a food, and other samples capable of containing or harboring heterogeneous microbial samples.

A. Diagnostics and Therapeutics

The resulting reports can be used for diagnostic and therapeutic purposes. For example, analysis of the microbiota of a sample may indicate the presence of pathogenic microorganisms. Alternatively, the analysis may indicate an imbalance in different kinds of microorganisms. These situations can be addressed therapeutically. For example, therapeutic interventions may be instituted to eliminate pathogenic microorganisms. Alternatively, if the microbiota is determined to be imbalanced, microorganisms can be introduced into the subject to mitigate this imbalance.

In another embodiment information can be used to diagnose pathologic conditions. For example, subjects having a particular pathologic state can be analyzed for contents and activity of their microbiota from designated samples. Information from these analyses can, in turn, be analyzed to find correlations between particular microbiota profiles and the disease state. These profiles can then be used to diagnose the state.

Heterogeneous microbial samples can include those obtained from a subject. For example, the sample can comprise earwax, sweat, breast milk, hair, blood, bile, cerebrospinal fluid, lymphatic fluid, semen, vaginal discharge, menstrual fluid, feces, sputum, urine, saliva, secretions from open wounds, secretions from the eye, skin tissue, a skin biopsy, subcutaneous tissue, muscle tissue, adipose tissue, and a combination thereof, obtained from a subject.

Such methods can also be used to detect the presence of bacteria used in a bioterrorism attacks in heterogeneous microbial samples.

B. Environmental Remediation

The resulting reports can be used for environmental remediation purposes. Bioremediation, for example, can treat a polluted area either by altering environmental conditions to stimulate growth of microorganisms or through natural microorganism activity, resulting in the degradation of the target pollutants. The methods, systems and databases used herein can assess or monitor the composition of the microbial communities present in contaminated locations or materials. These assessments can be used to identify the contaminants present and the progress of the remediation.

V. COMPUTER SYSTEMS

The methods described herein may be used in the context of a computer system or as part of software or computer-executable instructions that are stored in a computer-readable storage medium.

Reference is made throughout this disclosure to various advantages and performance improvements the present methods, databases, and systems have over existing systems. In some aspects, a size of a database according to this disclosure is reduced by 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 60%, 70%, 80%, 90%, 95%, 96%, 97%, 98%, 99%, 99.5%, or 99.9% compared to databases that is not in accordance with this disclosure.

In some aspects, the amount of memory to run the sequence signature generation analysis is reduced by 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 60%, 70%, 80%, 90%, 95%, 96%, 97%, 98%, 99%, 99.5%, or 99.9% compared to an analysis that is not in accordance with this disclosure.

In some aspects, the number of CPU cycles to run the sequence signature generation analysis is reduced by 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 60%, 70%, 80%, 90%, 95%, 96%, 97%, 98%, 99%, 99.5%, or 99.9% compared to an analysis that is not in accordance with this disclosure.

In some aspects, the amount of time to run the methods described herein is reduced by 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 60%, 70%, 80%, 90%, 95%, 96%, 97%, 98%, 99%, 99.5%, or 99.9% compared to a method that is not in accordance with this disclosure.

In some aspects, the number of CPU cycles to run the sequence signature sample analysis is reduced by 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 60%, 70%, 80%, 90%, 95%, 96%, 97%, 98%, 99%, 99.5%, or 99.9% compared to an analysis that is not in accordance with this disclosure.

In some aspects, the number of alignments to run the sequence signature sample analysis is reduced by 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 60%, 70%, 80%, 90%, 95%, 96%, 97%, 98%, 99%, 99.5%, or 99.9% compared to an analysis that is not in accordance with this disclosure.

In some aspects, the number of CPU cycles to run the sequence signature sample analysis is reduced by 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 60%, 70%, 80%, 90%, 95%, 96%, 97%, 98%, 99%, 99.5%, or 99.9% compared to an analysis that is not in accordance with this disclosure.

In some aspects, the amount of memory to run the sequence signature sample analysis is reduced by 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 60%, 70%, 80%, 90%, 95%, 96%, 97%, 98%, 99%, 99.5%, or 99.9% compared to an analysis that is not in accordance with this disclosure.

In some embodiments, a system (e.g., a computer system) may be used to implement certain features of some of the embodiments of the invention. For example, in certain embodiments, a system (e.g., a computer system) for large scale metagenomic analysis of heterogeneous microbial populations in a sample is provided. The analysis performed by the system may be used in accordance with the features of the embodiments described above.

In certain embodiments, the system may include one or more memory and/or storage devices. The memory and storage devices may be one or more computer-readable storage media that may store computer-executable instructions that implement at least portions of the various embodiments of the invention. In one embodiment, the system may include a computer-readable storage medium which stores computer-executable instructions that include, but are not limited to, one or both of the following: instructions for generating a database comprising sequence signatures for at least one organism from at least one taxon; instructions for analyzing sequence reads obtained from a sample for sequence signatures informative of taxonomic information; and instructions for analyzing sequence reads obtained from a sample for determining the presence of a biochemical activity present in the sample. Such instructions may be carried out in accordance with the methods described in the embodiments above.

In certain embodiments, the system may include a processor configured to perform one or more steps including, but not limited to, (i) receiving at least one input file or accessing at least one database and (ii) executing the computer-executable instructions stored in the computer-readable storage medium. The set of input files may include, but is not limited to, a file that includes a set of reads generated by sequencing nucleic acids from a sample comprising a heterogeneous population of microbes. The steps may be performed in accordance with the methods described in the embodiments above.

The computer system may be a server computer, a client computer, a personal computer (PC), a user device, a tablet PC, a laptop computer, a personal digital assistant (PDA), a cellular telephone, an iPhone, an iPad, a Blackberry, a processor, a telephone, a web appliance, a network router, switch or bridge, a console, a hand-held console, a (hand-held) gaming device, a music player, any portable, mobile, hand-held device, wearable device, or any machine capable of executing a set of instructions, sequential or otherwise, that specify actions to be taken by that machine.

The computing system may include one or more central processing units ("processors"), memory, input/output devices, e.g. keyboard and pointing devices, touch devices, display devices, storage devices, e.g. disk drives, and network adapters, e.g. network interfaces, that are connected to an interconnect.

According to some aspects, the interconnect is an abstraction that represents any one or more separate physical buses, point-to-point connections, or both, connected by appropriate bridges, adapters, or controllers. The interconnect, therefore, may include, for example a system bus, a peripheral component interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus, also referred to as Firewire.

In addition, data structures and message structures may be stored or transmitted via a data transmission medium, e.g. a signal on a communications link. Various communications links may be used, e.g. the Internet, a local area network, a wide area network, or a point-to-point dial-up connection. Thus, computer readable media can include computer-readable storage media, e.g. non-transitory media, and computer-readable transmission media.

The instructions stored in memory can be implemented as software and/or firmware to program one or more processors to carry out the actions described above. In some embodiments of the invention, such software or firmware may be initially provided to the processing system by downloading it from a remote system through the computing system, e.g. via the network adapter.

The various embodiments of the disclosure introduced herein can be implemented by, for example, programmable circuitry, e.g. one or more microprocessors, programmed with software and/or firmware, entirely in special-purpose hardwired, e.g. non-programmable, circuitry, or in a combination of such forms. Special purpose hardwired circuitry may be in the form of, for example, one or more ASICs, PLDs, FPGAs, etc.

Some portions of the detailed description may be presented in terms of algorithms, which may be symbolic representations of operations on data bits within a computer memory. These algorithmic descriptions and representations are those methods used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

The algorithms and displays presented herein are not inherently related to any particular computer or other apparatus. Various general purpose systems may be used with programs in accordance with the teachings herein, or it may prove convenient to construct more specialized apparatus to perform the methods of some embodiments.

Moreover, while embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Further examples of machine-readable storage media, machine-readable media, or computer-readable (storage) media include but are not limited to recordable type media such as volatile and non-volatile memory devices, floppy and other removable disks, hard disk drives, optical disks (e.g., Compact Disk Read-Only Memory (CD ROMS), Digital Versatile Disks, (DVDs), etc.), among others, and transmission type media such as digital and analog communication links.

Figure 11:
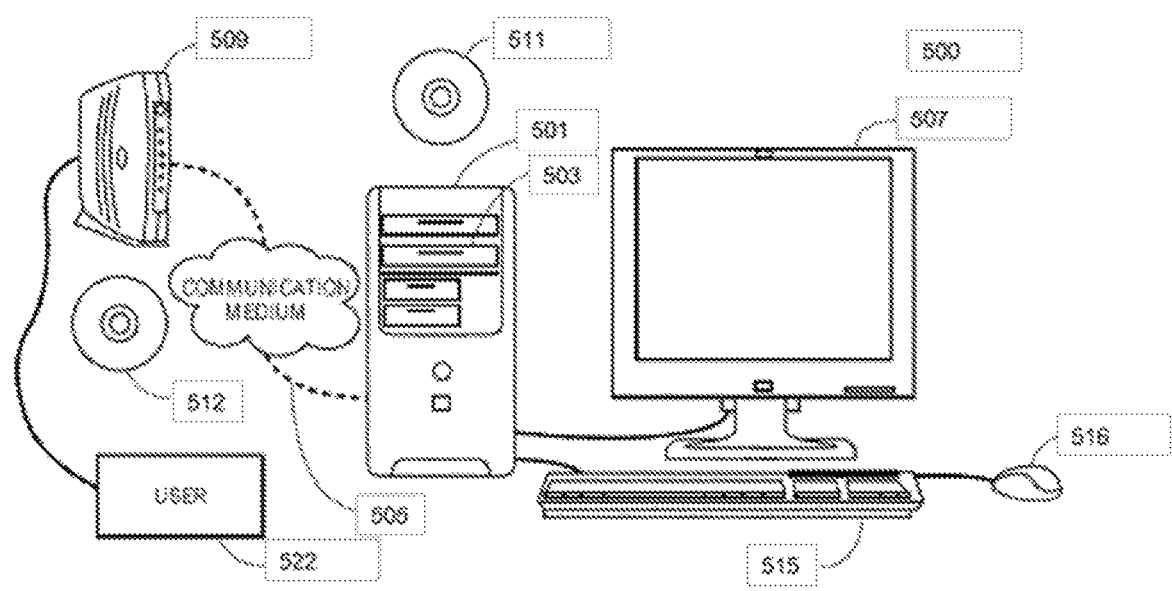
FIG. 11 illustrates various components of an exemplary computer system that can be programmed or configured to implement the methods provided herein.

Exemplary systems are provided herein. The computer system 500 illustrated in FIG. 11 may be understood as a logical apparatus that can read instructions from media 511 and/or a network port 505, which is optionally connected to server 509 having fixed media 512. In some cases, the system, such as shown in FIG. 11 includes a CPU 501, disk drives 503, optional input devices such as keyboard 515 and/or mouse 516 and optional monitor 507. In certain cases, data communication is achieved through the indicated communication medium to a server at a local or a remote location. In further cases, the communication medium includes any means of transmitting and/or receiving data. In some cases, the communication medium is a network connection, a wireless connection or an internet connection. In certain examples, such a connection provides for communication over the World Wide Web. It is envisioned that data relating to the present disclosure can be transmitted over such networks or connections for reception and/or review by a party 522 as illustrated in FIG. 11.

Figure 5:
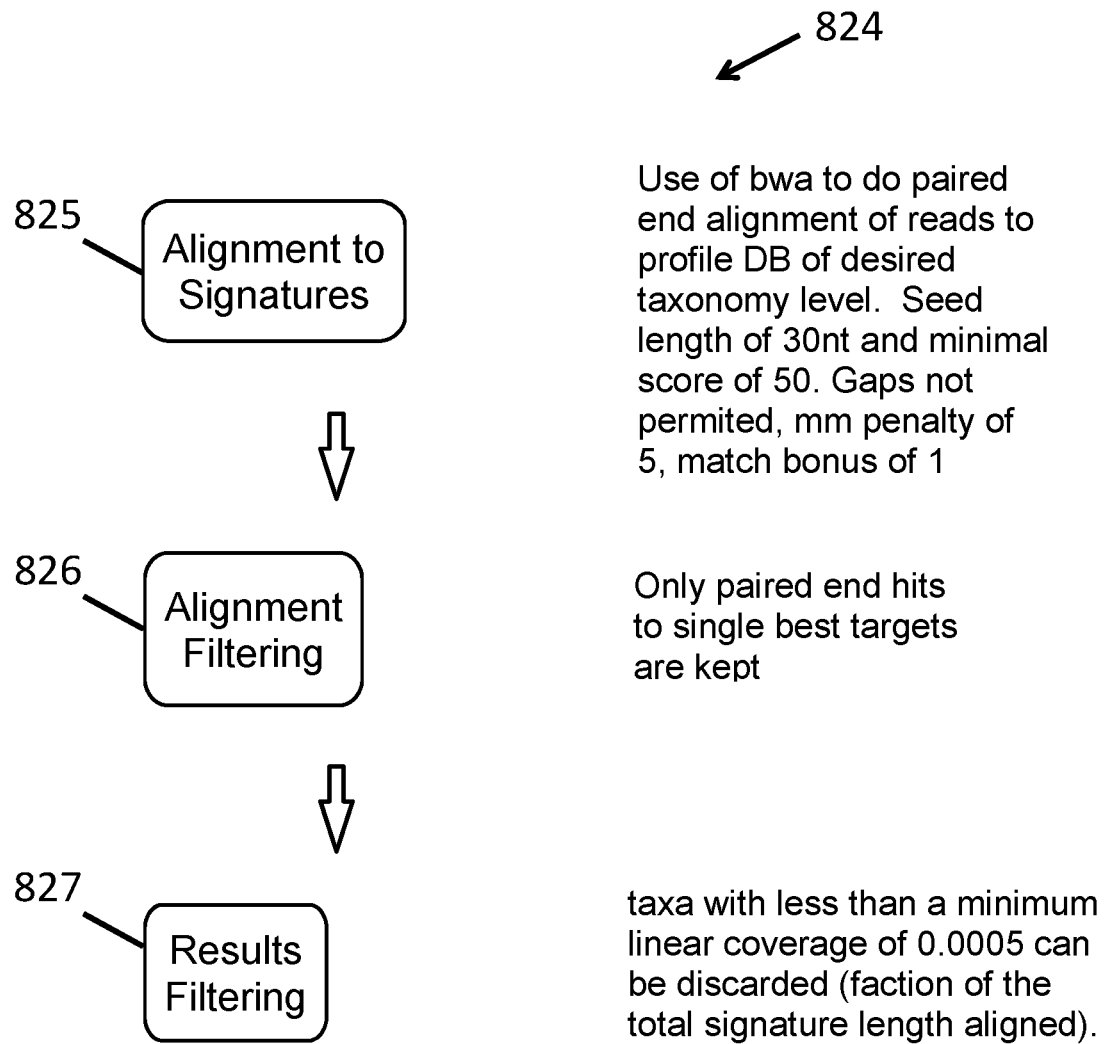
FIG. 5 shows a method for taxonomic identification.
Figure 12:
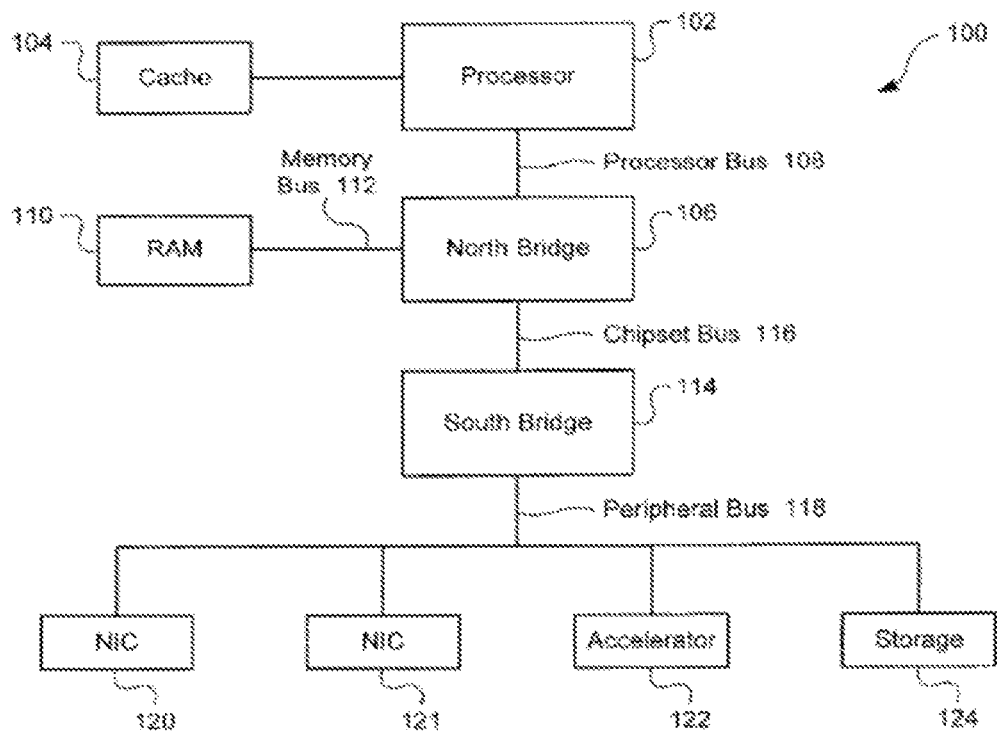
FIG. 12 is a block diagram illustrating the architecture of an exemplary computer system that can be programmed or configured to implement the methods provided herein.

FIG. 12 is a block diagram illustrating a first example architecture of a computer system 100 that can be used in connection with example embodiments of the present disclosure. In certain cases, as depicted in FIG. 5, the example computer system includes a processor 102 for processing instructions. Non-limiting examples of processors include: Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some embodiments, multiple processors or processors with multiple cores are used, whether in a single computer system, in a cluster, or distributed across systems over a network comprising a plurality of computers, cell phones, and/or personal data assistant devices.

In various cases, as illustrated in FIG. 12, a high speed cache 104 is connected to, or incorporated in, the processor 102 to provide a high speed memory for instructions or data that have been recently, or are frequently, used by processor 102. The processor 102 is connected to a north bridge 106 by a processor bus 108. The north bridge 106 is connected to random access memory (RAM) 110 by a memory bus 112 and manages access to the RAM 110 by the processor 102. The north bridge 106 is also connected to a south bridge 114 by a chipset bus 116. The south bridge 114 is, in turn, connected to a peripheral bus 118. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 118. In some alternative architectures, the functionality of the north bridge can be incorporated into the processor instead of using a separate north bridge chip.

In some embodiments, system 100 includes an accelerator card 122 attached to the peripheral bus 118. In some cases, the accelerator includes field programmable gate arrays (FPGAs) or other hardware for accelerating certain processing. In further examples, an accelerator is used for adaptive data restructuring or to evaluate algebraic expressions used in extended set processing.

Software and data are stored in external storage 124 and can be loaded into RAM 110 and/or cache 104 for use by the processor. The system 100 includes an operating system for managing system resources; non-limiting examples of operating systems include: Linux, Windows™, MACOS™, BlackBerry OS™, iOS™, Android™, and other functionally-equivalent operating systems, as well as application software running on top of the operating system for managing data storage and optimization in accordance with example embodiments of the present disclosure.

In this example, system 100 also includes network interface cards (NICs) 120 and 121 connected to the peripheral bus for providing network interfaces to external storage, such as Network Attached Storage (NAS) and other computer systems that can be used for distributed parallel processing.

Figure 13:
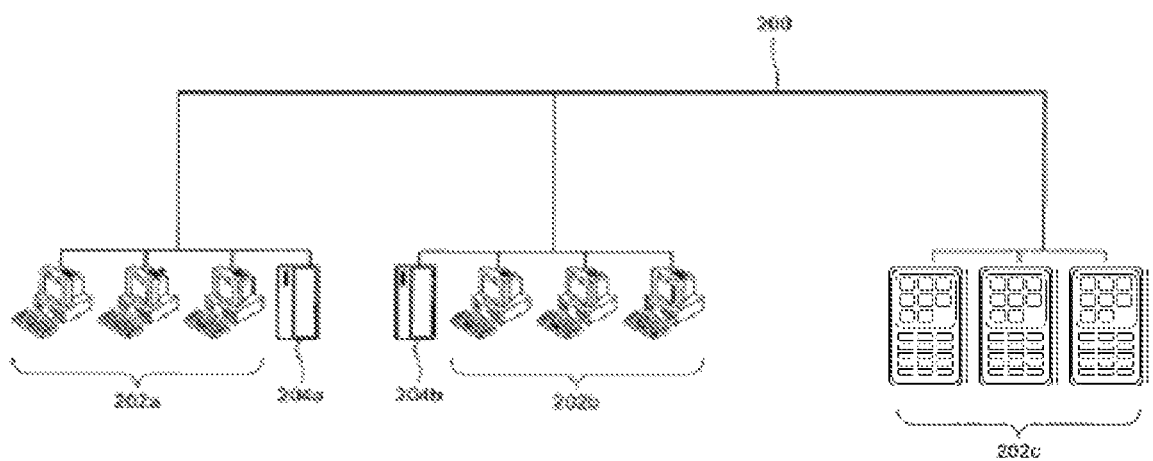
FIG. 13 is a diagram illustrating an exemplary computer network that can be configured to implement the methods provided herein.

FIG. 13 is a diagram showing a network 200 with a plurality of computer systems 202a, and 202b, a plurality of cell phones and personal data assistants 202c, and Network Attached Storage (NAS) 204a, and 204b. In certain examples, systems 202a, 202b, and 202c manage data storage and optimize data access for data stored in Network Attached Storage (NAS) 204a and 204b. In some cases, a mathematical model is used for the data and evaluated using distributed parallel processing across computer systems 202a, and 202b, and cell phone and personal data assistant systems 202c. In certain cases, computer systems 202a, and 202b, and cell phone and personal data assistant systems 202c also provide parallel processing for adaptive data restructuring of the data stored in Network Attached Storage (NAS) 204a and 204b. FIG. 13 illustrates an example only, and a wide variety of other computer architectures and systems are used in conjunction with the various embodiments of the present disclosure. In some cases, a blade server is used to provide parallel processing. In further examples, processor blades are connected through a back plane to provide parallel processing. In certain examples, storage is connected to the back plane or as Network Attached Storage (NAS) through a separate network interface.

In some cases, processors maintain separate memory spaces and transmit data through network interfaces, back plane or other connectors for parallel processing by other processors. In other embodiments, some or all of the processors use a shared virtual address memory space.

Figure 14:
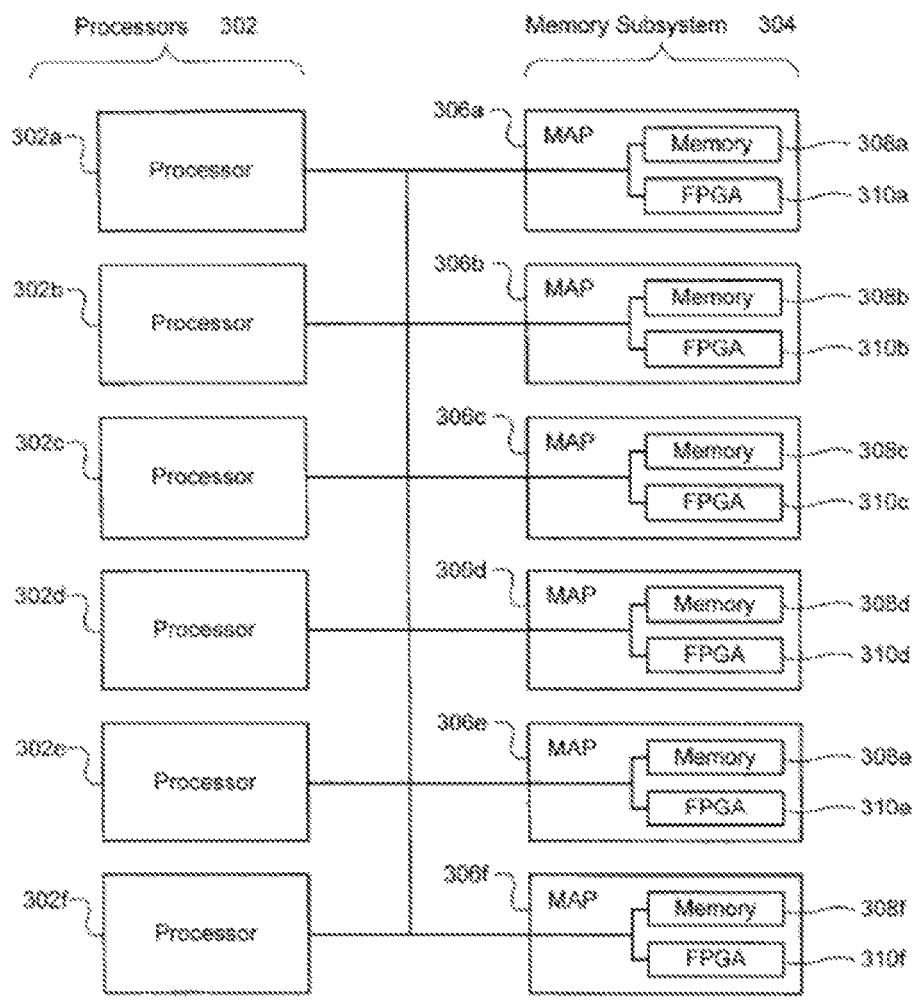
FIG. 14 is a block diagram illustrating the architecture of another exemplary computer system that can be programmed or configured to implement the methods provided herein.

FIG. 14 is a block diagram of a multiprocessor computer system 300 using a shared virtual address memory space in accordance with an example embodiment. The system includes a plurality of processors 302a-f that can access a shared memory subsystem 304. The system incorporates a plurality of programmable hardware memory algorithm processors (MAPs) 306a-f in the memory subsystem 304. In some cases, each MAP 306a-f comprises a memory 308a-f and one or more field programmable gate arrays (FPGAs) 310a-f. The MAP provides a configurable functional unit and particular algorithms or portions of algorithms can be provided to the FPGAs 310a-f for processing in close coordination with a respective processor. In some cases, the MAPs are used to evaluate algebraic expressions regarding the data model and to perform adaptive data restructuring in example embodiments. In this example, each MAP is globally accessible by all of the processors for these purposes. In one configuration, each MAP uses Direct Memory Access (DMA) to access an associated memory 308a-f, allowing it to execute tasks independently of, and asynchronously from, the respective microprocessor 302a-f In this configuration, a MAP feeds results directly to another MAP for pipelining and parallel execution of algorithms.

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

In some embodiments, the platforms, systems, media, and methods disclosed herein include one or more databases, or use of the same. In view of the disclosure provided herein, those of skill in the art will recognize that many databases are suitable for storage and retrieval of sequencing, sequence signature, genomic, and taxonomic information. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

The above computer architectures and systems are examples only, and a wide variety of other computer, cell phone, and personal data assistant architectures and systems can be used in connection with exemplary embodiments, including systems using any combination of general processors, co-processors, FPGAs and other programmable logic devices, system on chips (SOCs), application specific integrated circuits (ASICs), and other processing and logic elements. In some embodiments, all or part of the computer system is implemented in software or hardware. In certain cases, any variety of data storage media is used in connection with example embodiments, including random access memory, hard drives, flash memory, tape drives, disk arrays, Network Attached Storage (NAS) and other local or distributed data storage devices and systems.

In some cases, the computer system is implemented using software or hardware modules executing on any of the above or other computer architectures and systems. In other embodiments, the functions of the system are implemented partially or completely in firmware, programmable logic devices such as field programmable gate arrays (FPGAs) as referenced in FIG. 14, system on chips (SOCs), application specific integrated circuits (ASICs), or other processing and logic elements. In some cases, the Set Processor and Optimizer is implemented with hardware acceleration through the use of a hardware accelerator card, such as accelerator card 122 illustrated in FIG. 12.

VI. DEFINITIONS AND FIGURES

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

The RNA includes, but is not limited to, mRNAs, tRNAs, snRNAs, rRNAs, retroviruses, small non-coding RNAs, microRNAs, polysomal RNAs, pre-mRNAs, intronic RNA, viral RNA, cell free RNA and fragments thereof. The non-coding RNA, or ncRNA can include snoRNAs, microRNAs (miRNAs), siRNAs, piRNAs and long nc RNAs.

The nucleic acid molecules are often contained within at least one biological cell. Alternately, the nucleic acid molecules are contained within a noncellular biological entity, such as, for example, a virus or viral particle. Nucleic acid molecules are often constituents of a lysate of a biological cell or entity. Nucleic acid molecules are often profiled within a single biological cell or a single biological entity. Alternately, nucleic acid molecules are profiled in a lysate obtained from a single biological cell or a single biological entity. The source of nucleic acid for use in the methods and compositions described herein are often a sample comprising the nucleic acid.

As used herein, the term "about" a number refers to a range spanning that number plus or minus 10% of that number. The term "about" a range refers to that range minus 10% of its lowest value and plus 10% of its greatest value.

As used here, the terms "comprise," "comprises," "comprising," "include," "includes," and "including" are interchangeable and not intended to be limiting, and refer to the nonexclusive presence of the recited element, leaving open the possibility that additional elements are present.

As used herein, the term "comparable to" a number refers to that number plus or minus 50% of that number. The term "comparable to" a range refers to that range minus 50% of its lowest value and plus 50% of its greatest value.

As used herein, the term "subject", refers to any individual or patient to which the subject methods are performed. Generally the subject is human, although as will be appreciated by those in the art, the subject may be any organism, including an animal or plant or microbe. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

As used herein, "obtaining" a nucleic acid sample is given a broad meaning in some cases, such that it refers to receiving an isolated nucleic acid sample, as well as receiving a raw human or environmental sample, for example, and isolating nucleic acids therefrom.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

Turning to the figures, FIG. 1 is a diagram of an exemplary method in accordance with an embodiment of the present disclosure. The method 800 starts. 801 represents genome fetching. This step includes "download all complete and draft genomes from RefSeq and NCBI FTP sites. 802 represents genome cleaning. This step includes "Identify and remove all contaminating sequences such as phages, plasmids, spurious sequences from the saved genome database." 803 represents redundancy removal. This step includes "Identify and remove dumplicate genomes that represent the same strain." 804 represents taxonomic tree construction. This step includes "Taxonomic Tree is updated to reflect any changes induced from the above step." 805 represents curated genomes. This step includes "Save database of curated genomes and use as input for the next step." There are arrows from each step to the next step.

Figure 2:
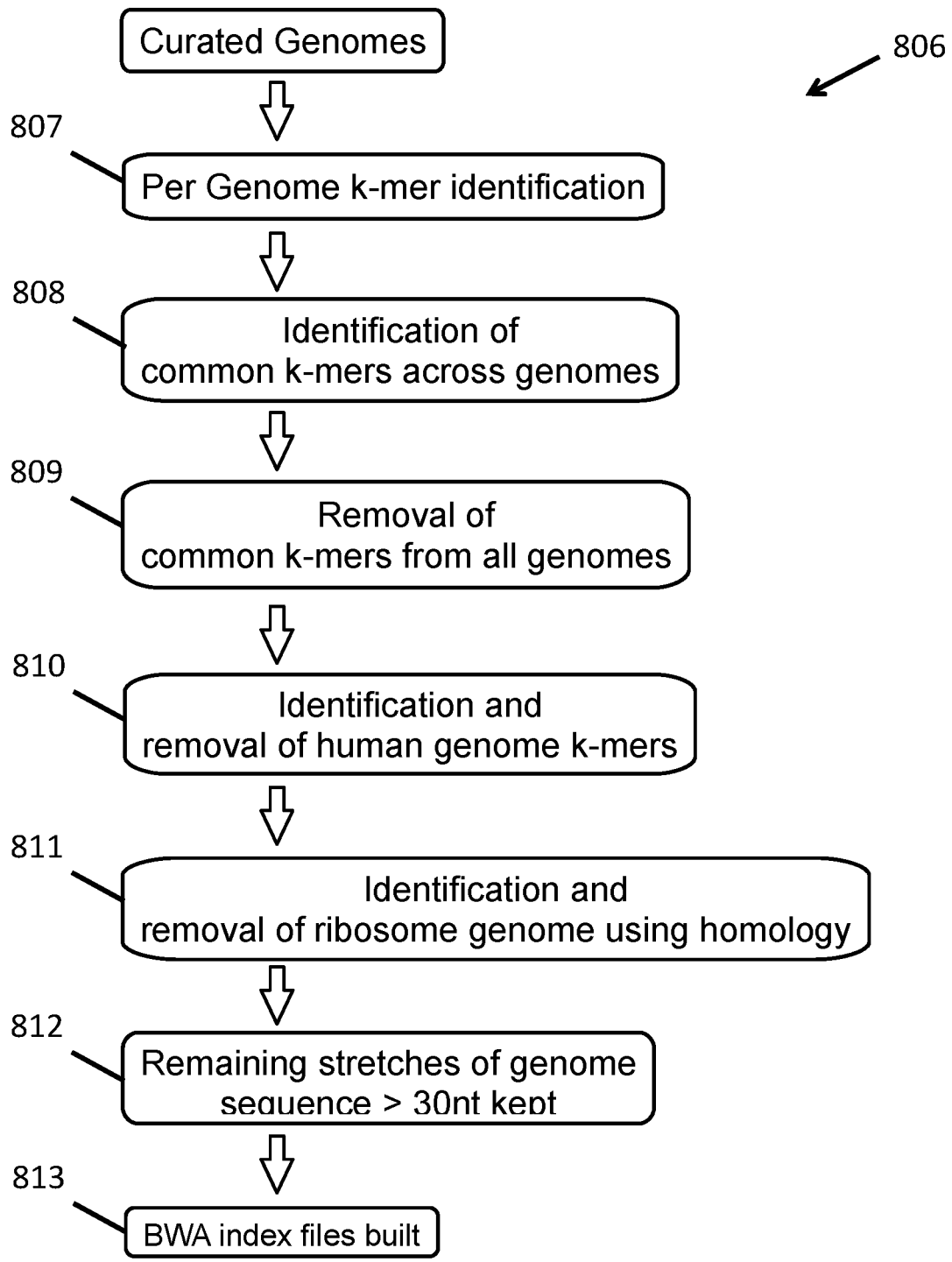
FIG. 2 shows a method of constructing taxonomic signatures.

FIG. 2 is a diagram of an exemplary method 806 in accordance with an embodiment of the present disclosure. The curated genomes are represented by the first box. 807: Per genome k-mer identification. 808: Identification of common k-mers across genomes. 809: removal of common k-mers from all genomes. 810: Identification and removal of human genome k-mers. Steps 807-810 can be done in parallel or in sequence. If done in sequence, the sequence can be in the order depicted or any other order. 811: Identification and removal of ribosome genome using homology. The use of k-n-mers is also contemplated. 812: Remaining stretches of genome sequence>30 nt kept. 813: BWA index files built. There are arrows from each step to the next step.

Figure 3:
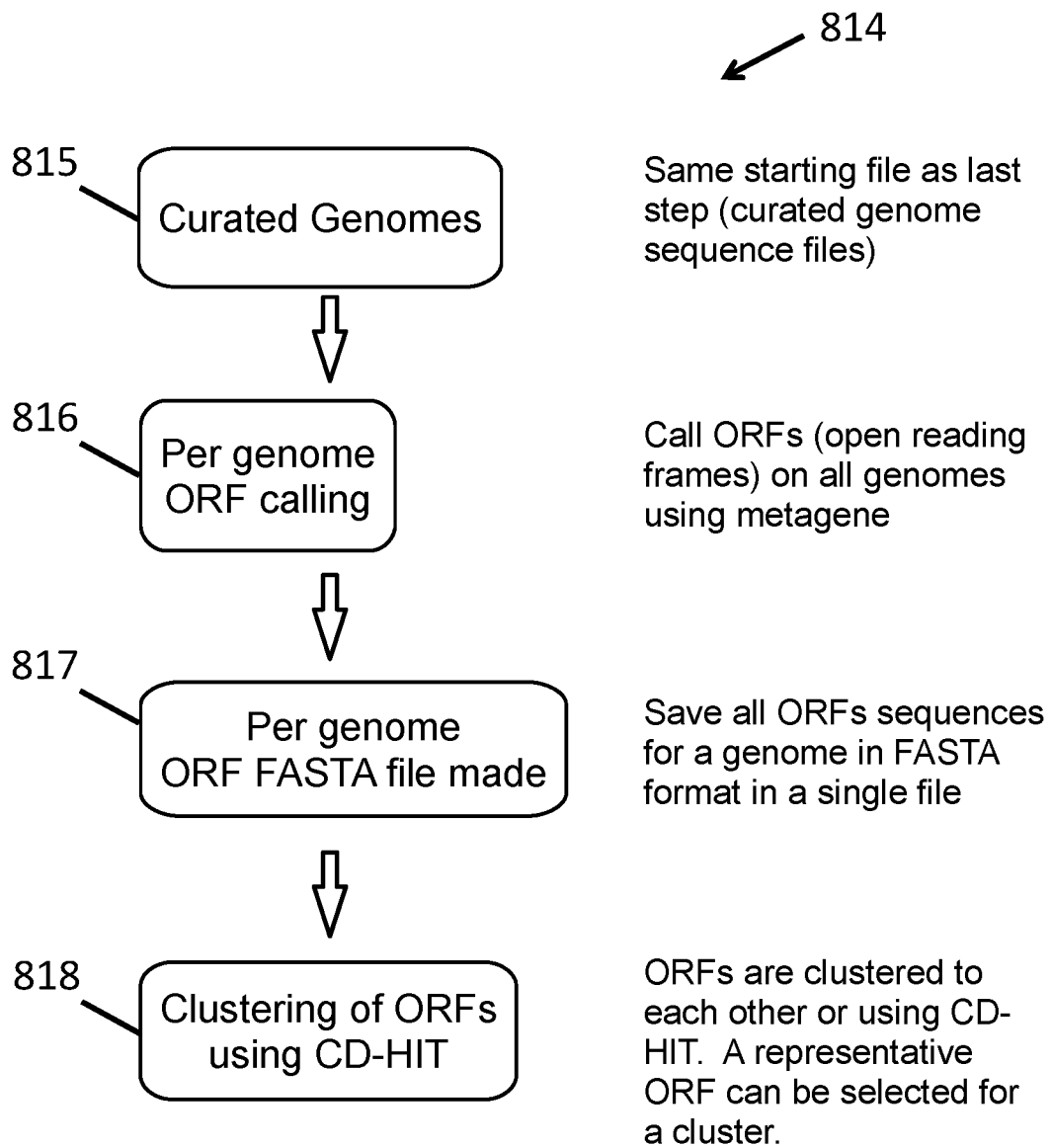
FIG. 3 shows a method of creating full genome open reading frame libraries.

FIG. 3 is a diagram of an exemplary method 814 in accordance with an embodiment of the present disclosure. 815 represents curated genomes. This step includes "Same starting file as last step (curated genome sequence files). 816 represents per genome ORF calling. This step includes "call ORFs (open reading frames) on all genomes using metagene." 817 represent "Per genome ORF FASTA file made." This step includes "Save all ORFs sequences for a genome in FASTA format in a single file. 818 Represents clustering ORFs using CH-HIT. ORFs are clustered to each other or using CD-HIT. A representative ORF can be selected for a cluster. Mapping of ORFs to IGC is also contemplated. This step includes "Map genes from each gene file to IGC (integrated gene catalog) using CD-hit. Allows rapid annotation down stream. There are arrows from each step to the next step.

Figure 4:
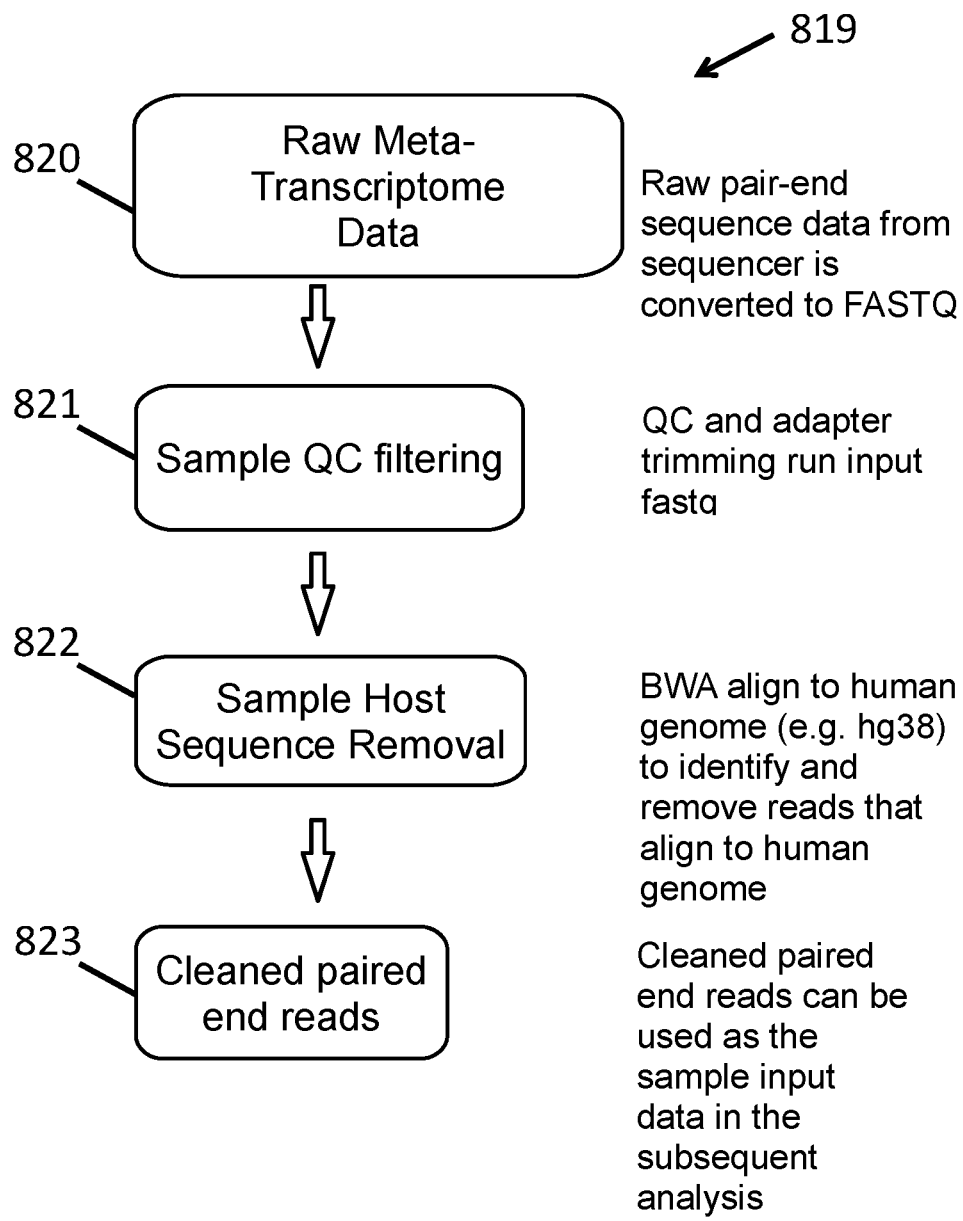
FIG. 4 shows a method of preprocessing sequence reads.

FIG. 4 is a diagram of an exemplary method 819 in accordance with an embodiment of the present disclosure. 820 represents raw meta-transcriptome data. This step includes "Raw pair-end sequence data from sequencer is converted to FSATQ. 821 represents sample QC filtering. This step includes "pretty standard QC and adapter trimming run input fastq." 822 represents sample host sequence removal. This step includes "BWA align to human genome (hg38) to identify and remove reads that align to human genome." 823 represents cleaned paired-ends reads. This step is the input into ViOmega (an exemplary embodiment of the disclosure) from the sample side. There are arrows from each step to the next step.

FIG. 5 is a diagram of an exemplary method 824 in accordance with an embodiment of the present disclosure. 825 represents alignment to signatures. This step includes "Use of bwa to do paired-end alignment of reads to profile DB of designed taxonomy level. Seed length of 30 nt and minimal score of 50. Gaps not permitted, mm penalty of 5, match bonus of 1." Minimal scores of less than 50 are also contemplated, such as 30. 826 represents alignment filtering. This step includes "Only paired-end hits to single best target are kept." 827 represents results filtering. The step includes "Viomega 2 defaults (an exemplary embodiment of the disclosure): Only Taxon with >3 read hits and linear length of >60 nt and >0.005 fractional abundance are kept. Taxa with less than a minimum linear coverage of 0.0005 can be discarded (faction of the total signature length aligned)."

Figure 6:
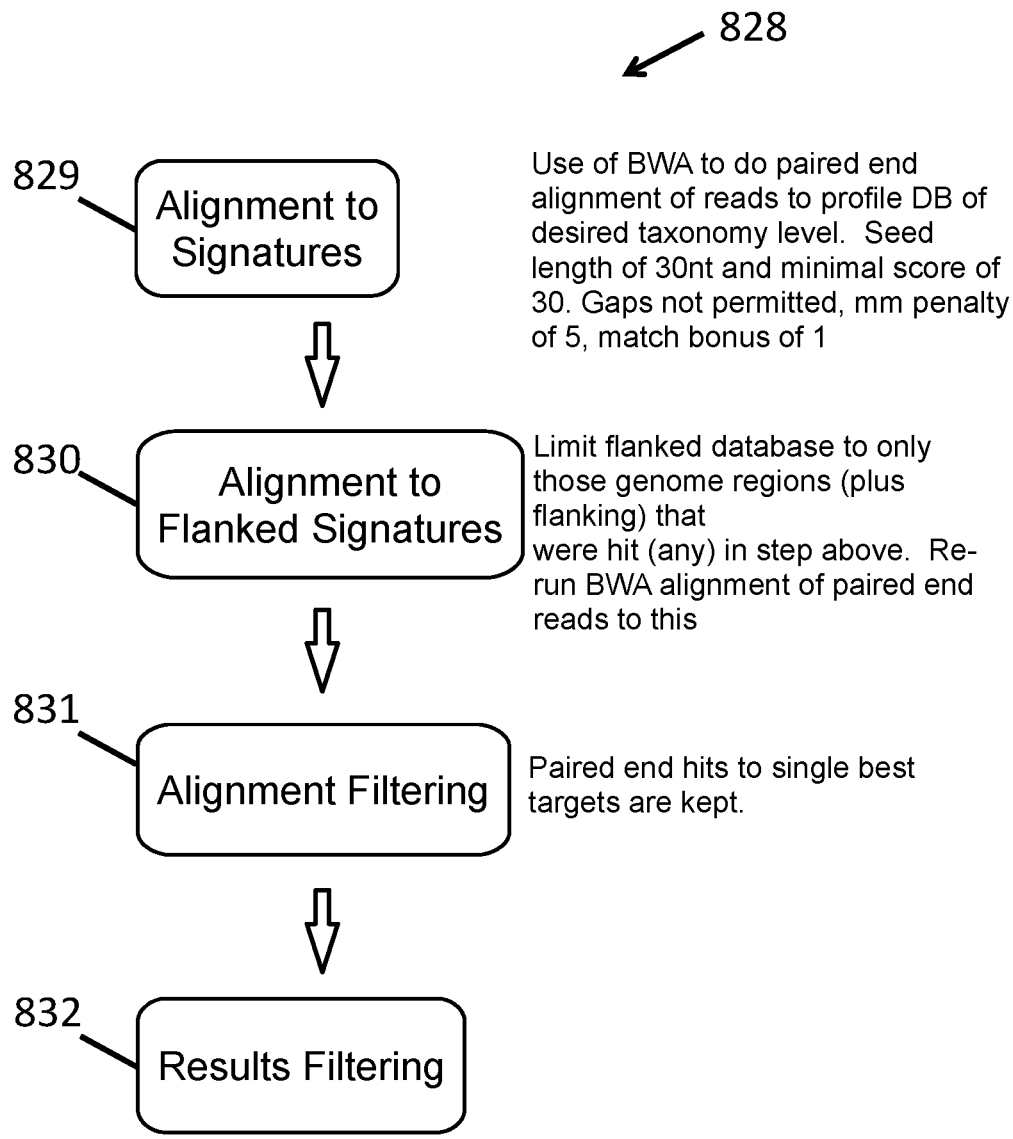
FIG. 6 shows a method for taxonomic identification using genomic flanking sequences.

FIG. 6 is a diagram of an exemplary method 828 in accordance with an embodiment of the present disclosure. 829 represents alignment to signatures. This step includes "Use of BWA to do paired-end alignment of reads to profile DB of desired taxonomy level. Seed length of 30 nt and minimal score of 30. Gaps not permitted, mm penalty of 5, match bonus of 1." 830 represents alignment to flanked signatures. This step includes "Limit flanked database to only those genome regions (plus flanking) that were hit (any) in step above. Re-run BWA alignment of paired-end reads to this." 831 represents alignment filtering. This step includes "Only paired-end hits to single best targets are kept. Conceptually similar to what is done in Gottcha 2, but run an a somewhat different file output." 832 represents results filtering. There are arrows from each step to the next step.

Figure 7:
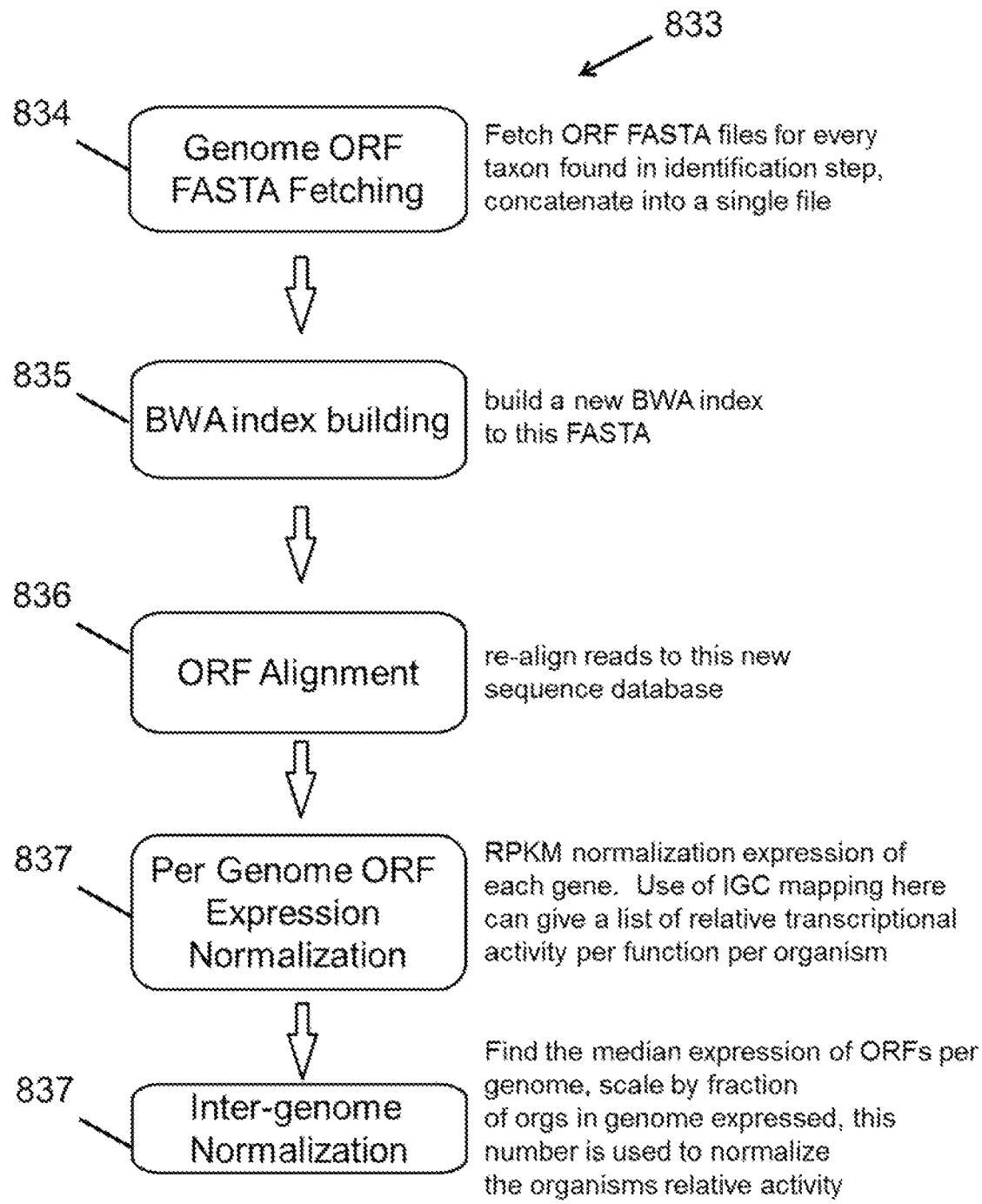
FIG. 7 shows a method of taxonomic quantification.

FIG. 7 is a diagram of an exemplary method 833 in accordance with an embodiment of the present disclosure. 834 represents Genome ORF FASTA fetching. This step includes "Fetch ORF FASTA files for every taxon found in identification step, concatenate into a single file." 835 represents BWAS index building. This step includes "build a new BWA index to this FASTA." 836 includes ORF Alignment. This step includes "re-align all reads to this new sequence database." 837 represents Per Genome ORF Expression Normalization. This step includes "RPKM normalization expression of each gene. Use of IGC mapping here can give a list of relative transcriptional activity per function per organism." 837, which is a separate 837 than above, represents Inter-genome Normalization. This step includes "Find the median expression of ORFs per genome, scale by fraction of orgs in genome expressed, this number is used to normalize the organisms relative activity."

FIG. 8 shows tabular results obtained from an analysis of a commercially available microbial community standard sample (ZymoBIOMICS from Zymo Research), in which the results shown indicate which samples were identified according to embodiments of the present disclosure and their relative abundance and comparing to results obtained using the GOTTCHA and mOTUs metagenomics profiling tools.

The standard sample contained a single species of *Lactobacillus*, which was *Lactobacillus fermentum*. GOTTCHA inaccurately identified three *Lactobacillus* species as being present in the sample, two of which, *Lactobacillus buchneri* and *Lactobacillus johnsonii*, were false positives. In contrast, ViOmega, a system in accordance with various embodiments of the present disclosure, correctly identified that the sample only contained *Lactobacillus fermentum*. * denotes false positive results. † denotes false negative results.

Figure 9A:
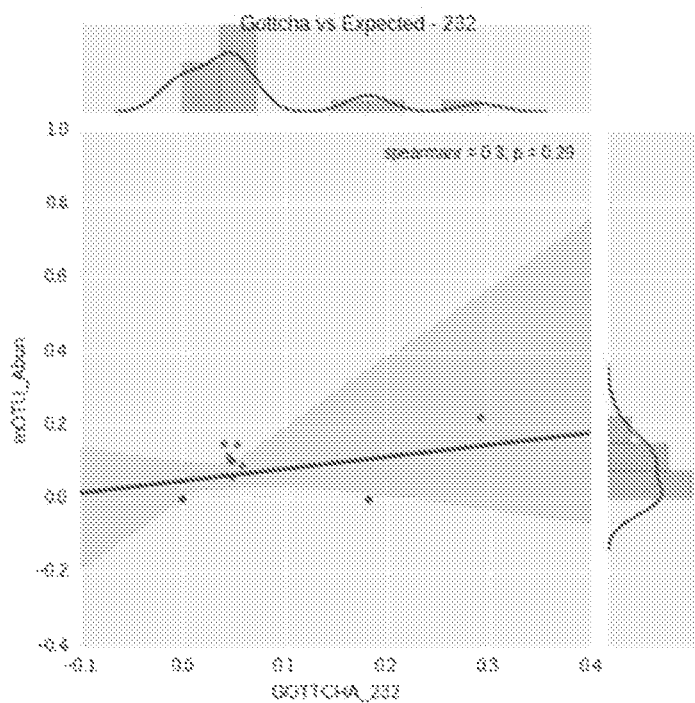
FIG. 9A is a graph of relative abundance of Zymo-BIOMICS community standard sample #232, representing the Spearman correlation between GOTTCHA and expected relative values from the known standard. GOTTCHA demonstrates lower correlation than methods shown herein.

FIG. 9A is a graph of relative abundance of Zymo-BIOMICS community standard sample #232, representing the Spearman correlation between GOTTCHA and expected relative values from the known standard. GOTTCHA demonstrates lower correlation than methods shown herein. For GOTTCHA, the Spearman correlation was 0.3 and p=0.29.

Figure 9B:
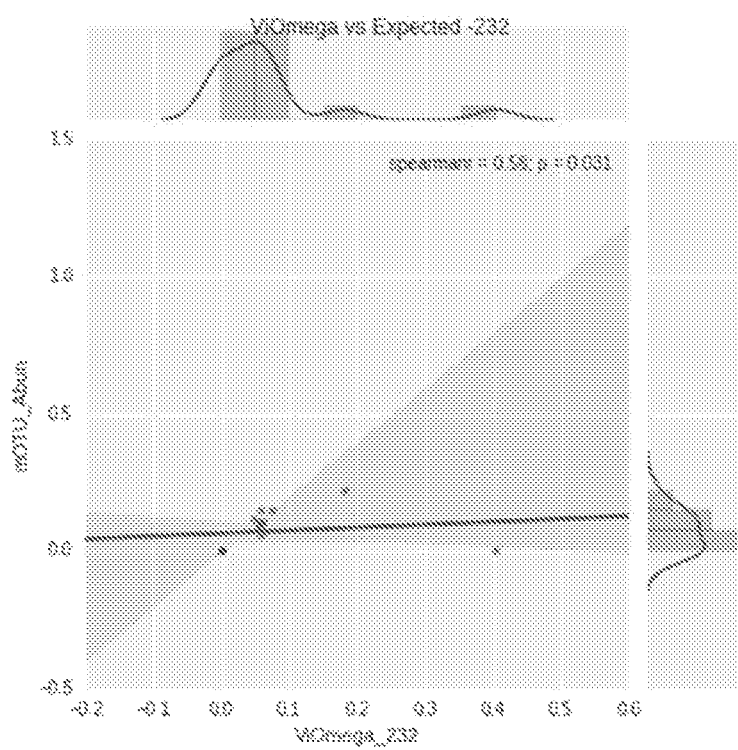
FIG. 9B is a graph of relative abundance of Zymo-BIOMICS community standard sample #232, according to embodiments of the present invention, representing the Spearman correlation between methods disclosed herein and expected relative values from the known standard. The methods described herein demonstrate stronger correlation than GOTTCHA.

FIG. 9B is a graph of relative abundance of Zymo-BIOMICS community standard sample #232, according to embodiments of the present invention, representing the Spearman correlation between methods disclosed herein and expected relative values from the known standard. The methods described herein demonstrate stronger correlation than GOTTCHA. The Spearman correlation was 0.58 and p=0.031.

Figure 10A:
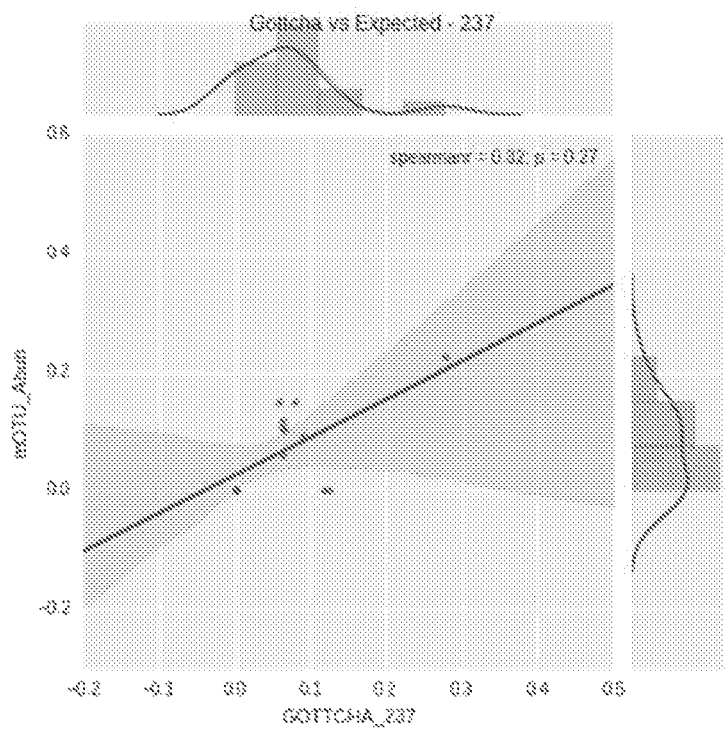
FIG. 10A is a graph of relative abundance of Zymo-BIOMICS community standard sample #237, representing the Spearman correlation between GOTTCHA and expected relative values from the known standard. GOTTCHA demonstrates lower correlation than methods described herein.

FIG. 10A is a graph of relative abundance of Zymo-BIOMICS community standard sample #237, representing the Spearman correlation between GOTTCHA and expected relative values from the known standard. GOTTCHA demonstrates lower correlation than methods described herein. The Spearman correlation was 0.32 and p=0.27.

Figure 10B:
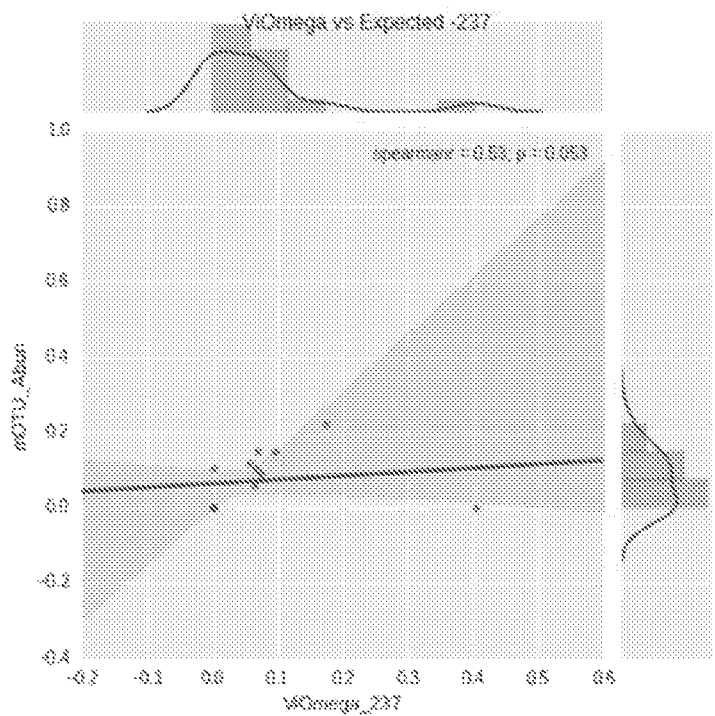
FIG. 10B is a graph of relative abundance of Zymo-BIOMICS community standard sample #237, according to embodiments of the present invention, representing the Spearman correlation between methods described herein and expected relative values from the known standard. Methods described herein demonstrate a stronger correlation than GOTTCHA.

FIG. 10B is a graph of relative abundance of Zymo-BIOMICS community standard sample #237, according to embodiments of the present invention, representing the Spearman correlation between methods described herein and expected relative values from the known standard. Methods described herein demonstrate a stronger correlation than GOTTCHA. The Spearman correlation was 0.53 and p=0.053.

VII. EXEMPLARY EMBODIMENTS

1. A method of taxonomically classifying organisms in a heterogeneous microbial sample comprising: obtaining ribonucleic acids from a heterogeneous microbial sample; obtaining sequence information representative of the ribonucleic acids; assaying for a presence of a sequence signature (e.g., one or more sequence signatures) in the heterogeneous microbial sample informative of a category of organisms; and categorizing the heterogeneous microbial sample as comprising an organism corresponding to the category (e.g., one or more categories) of organisms. 2. The method of embodiment 1, wherein the category of organisms is informative of a biochemical activity present in the sample. 3. The method of embodiment 2, wherein the biochemical activity is informative of a biochemical pathway present in the heterogeneous microbial sample. 4. The method of embodiment 1, further comprising quantifying the organism corresponding to the category of organisms. 5. The method of embodiment 4, wherein quantifying the organism comprises determining a depth of coverage for sequence signatures corresponding to the category of organisms relative to a total depth of coverage for sequence signatures present in the sample. 6. The method of embodiment 4, wherein quantifying the organism comprises determining a depth of coverage for sequence signatures corresponding to the category of organisms relative to a total depth of coverage for sequence signatures corresponding to other categories of organisms present in the sample. 7. The method of embodiment 4, wherein quantifying comprises determining a number of reads per kilobase corresponding to the category of organisms per million mapped reads. 8. The method of embodiment 1, wherein the method further comprises removing non-target ribonucleic acids from the sample prior to obtaining sequence information. 9. The method of embodiment 8, wherein the non-target ribonucleic acids comprises bacterial ribosomal RNA. 10. The method of embodiment 9, wherein the bacterial ribosome RNA comprises 16S RNA. 11. The method of embodiment 1, wherein the heterogeneous microbial sample is obtained from a host and the non-target ribonucleic acids comprise host RNA present in the sample. 12. The method of embodiment 1, wherein the method further comprises reverse transcribing the ribonucleic acids from the heterogeneous microbial sample into cDNA. 13. The method of embodiment 12, wherein obtaining sequence information comprises sequencing the cDNA. 14. The method of embodiment 13, wherein sequencing the cDNA comprises obtaining a plurality of sequence reads. 15. The method of embodiment 14, wherein assaying for the presence of the sequence signature does not comprise partitioning a sequence read of the plurality of sequence reads into a plurality of k-mers. 16. The method of embodiment 14, wherein assaying for the presence of the sequence signature comprises aligning the sequence signature to a sequence read of the plurality of sequence reads. 17. The method of embodiment 12, wherein the method further comprises removing a cDNA encoding a non-target nucleic acid from the sample prior to obtaining sequence information. 18. The method of embodiment 17, wherein the non-target cDNA encodes 16S RNA. 19. The method of embodiment 17, wherein the heterogeneous microbial sample is obtained from a host and the non-target cDNA encodes a host sequence. 20. The method of embodiment 1, wherein the heterogeneous microbial sample is obtained from a subject. 21. The method of embodiment 20, wherein the subject is human. 22. The method of embodiment 20, wherein the heterogeneous microbial sample comprises earwax, sweat, breast milk, hair, blood, bile, cerebrospinal fluid, lymphatic fluid, semen, vaginal discharge, menstrual fluid, feces, sputum, urine, saliva, secretions from open wounds, secretions from the eye, skin tissue, a skin biopsy, subcutaneous tissue, muscle tissue, adipose tissue, and a combination thereof. 23. The method of embodiment 22, wherein the heterogeneous microbial sample comprises feces. 24. The method of embodiment 1, wherein the heterogeneous microbial sample comprises soil. 24a. The method of embodiment 1, wherein assaying comprises mapping the sequence information to a library of taxonomic signatures. 24b. The method of embodiment 24a wherein the sequence information mapped comprises sequence information from forward and reverse reads of a paired-end read. 24c. The method of embodiment 24a wherein the library comprises taxonomic signatures for a plurality of different taxonomic levels.

25. A method of taxonomically classifying organisms in a heterogeneous microbial sample comprising: obtaining a ribonucleic acids from a heterogeneous microbial sample; obtaining sequence information representative of the ribonucleic acids; assaying for a presence of a sequence signature in the heterogeneous microbial sample informative of a taxon; and categorizing the heterogeneous microbial sample as comprising an organism corresponding to the taxon. 26. The method of embodiment 25, wherein assaying for a presence of a sequence signature in the heterogeneous microbial sample comprises assaying for a plurality of sequence signatures informative of a taxa. 27. The method of embodiment 26, wherein the sequence signature comprises nucleotide sequences unique to the taxon at a taxonomic rank. 28. The method of embodiment 25, wherein the taxon is informative of a biochemical pathway present in the heterogeneous microbial sample. 29. The method of embodiment 25, further comprising quantifying the organism corresponding to the taxon. 30. The method of embodiment 29, wherein quantifying the organism comprises determining a depth of coverage for sequence signatures corresponding to the taxon relative to a total depth of coverage for sequence signatures present in the sample. 31. The method of embodiment 29, wherein quantifying the organism comprises determining a depth of coverage for sequence signatures corresponding to the taxon relative to a depth of coverage for sequence signatures corresponding to other taxa present in the sample. 32. The method of embodiment 29, wherein quantifying comprises determining a number of reads per kilobase corresponding to the taxon per million mapped reads. 33. The method of embodiment 25, further comprising assaying the sequence information representative of the ribonucleic acids for a presence of an open reading frame encoded by a genome of the taxon. 34. The method of embodiment 33, wherein assaying the sequence information representative of the ribonucleic acids for a presence of an open reading frame encoded by a genome of the taxon comprises: identifying a genome from the taxon; identifying an open reading frame in the genome; and assaying for a presence of a sequence in the sequence information corresponding to the open reading frame. 35. The method of embodiment 33, further comprising quantifying ribonucleic acids corresponding to the open reading frame encoded by the genome of the taxon. 36. The method of embodiment 25, wherein the method further comprises removing non-target ribonucleic acids from the sample prior to obtaining sequence information. 37. The method of embodiment 36, wherein the non-target ribonucleic acids comprise 16S RNA. 38. The method of embodiment 36, wherein the heterogeneous microbial sample is obtained from a host and the non-target ribonucleic acids comprise host RNA present in the sample. 39. The method of embodiment 25, wherein the method further comprises reverse transcribing the ribonucleic acids from the heterogeneous microbial sample into cDNA. 40. The method of embodiment 39, wherein obtaining sequence information comprises sequencing the cDNA. 41. The method of embodiment 40, wherein sequencing the cDNA comprises obtaining a plurality of sequence reads. 42. The method of embodiment 41, wherein sequencing the cDNA comprises obtaining a plurality of single-end sequence reads. 43. The method of embodiment 41, wherein sequencing the cDNA comprises obtaining a plurality of paired-end sequence reads. 44. The method of embodiment 41, wherein assaying for a presence of a sequence signature does not comprise partitioning a sequence read of the plurality of sequence reads into a plurality of k-mers. 45. The method of embodiment 41, wherein assaying for the presence of the sequence signature comprises aligning the sequence signature to a sequence read of the plurality of sequence reads. 46. The method of embodiment 40, wherein the method further comprises removing a cDNA encoding a non-target nucleic acid from the sample prior to obtaining sequence information. 47. The method of embodiment 46, wherein the non-target cDNA encodes 16S RNA. 48. The method of embodiment 46, wherein the heterogeneous microbial sample is obtained from a host and the non-target cDNA encodes a host sequence. 49. The method of embodiment 25, wherein the heterogeneous microbial sample is obtained from a subject. 50. The method of embodiment 49, wherein the subject is human. 51. The method of embodiment 49, wherein the heterogeneous microbial sample comprises earwax, sweat, breast milk, hair, blood, bile, cerebrospinal fluid, lymphatic fluid, semen, vaginal discharge, menstrual fluid, feces, sputum, urine, saliva, secretions from open wounds, secretions from the eye, skin tissue, a skin biopsy, subcutaneous tissue, muscle tissue, adipose tissue, and a combination thereof. 52. The method of embodiment 51, wherein the heterogeneous microbial sample comprises feces. 53. The method of embodiment 25, wherein the heterogeneous microbial sample comprises soil. 53a. The method of embodiment 25, wherein assaying comprises mapping the sequence information to a library of taxonomic signatures. 53b. The method of embodiment 53a wherein the sequence information mapped comprises sequence information from forward and reverse reads of a paired-end read. 53c. The method of embodiment 53a wherein the library comprises taxonomic signatures for a plurality of different taxonomic levels. 53d. The method of embodiment 25 further comprising: providing a metagenomic open reading frame library; aligning sequences from the sequence information to the metagenomic open reading frame library; determining a measure of gene expression for each taxon identified in the sample; and outputting, for the sample, a quantitative measure (e.g., percent or relative amount) of microorganisms of one or more taxa or taxonomic levels, and optionally including relative expression levels of selected genes. 53e. The embodiment of method 53d comprising selecting from the library genomes corresponding to one or more taxa identified in the sample.

54. A method of taxonomically classifying organisms in a heterogeneous microbial sample comprising: obtaining sequencing reads representative of nucleic acids present in a heterogeneous microbial sample; assaying for a presence of a plurality of sequence signatures in the heterogeneous microbial sample informative of taxa, wherein the assaying does not comprise segmenting the paired-end reads into k-mer subsets and the plurality of sequence signatures is contained in a sequence signature database; and categorizing the heterogeneous microbial sample as comprising an organism corresponding to a taxon. 55. The method of embodiment 54, wherein the sequencing reads comprise single-end reads. 56. The method of embodiment 54, wherein the sequencing reads comprise paired-end reads. 57. The method of embodiment 54, wherein a sequence signature of the plurality of sequence signatures is informative of a taxon. 58. The method of embodiment 57, wherein a sequence signature comprises nucleotide sequences unique to the taxon at a taxonomic rank. 59. The method of embodiment 54, wherein the taxon is informative of a biochemical pathway present in the heterogeneous microbial sample. 60. The method of embodiment 54, further comprising quantifying the organism corresponding to the taxon. 61. The method of embodiment 60, wherein quantifying the organism comprises determining a depth of coverage for sequence signatures corresponding to the taxon relative to a total depth of coverage for sequence signatures present in the sample. 62. The method of embodiment 60, wherein quantifying the organism comprises determining a depth of coverage for sequence signatures corresponding to the taxon relative to a depth of coverage for sequence signatures corresponding to other taxa present in the sample. 63. The method of embodiment 60, wherein quantifying comprises determining a number of reads per kilobase corresponding to the taxon per million mapped reads. 64. The method of embodiment 54, wherein the method further comprises removing non-target nucleic acids from the sample prior to obtaining sequence information. 65. The method of embodiment 64, wherein the non-target nucleic acids comprise 16S RNA. 66. The method of embodiment 64, wherein the heterogeneous microbial sample is obtained from a host and the non-targetnucleic acids comprise host RNA present in the sample. 67. The method of embodiment 54, wherein obtaining sequence information comprises sequencing the nucleic acids. 68. The method of embodiment 67, wherein sequencing the nucleic acids comprises obtaining a plurality of sequence reads. 69. The method of embodiment 68, wherein assaying for a presence of a sequence signature does not comprise partitioning a sequence read of the plurality of sequence reads into a plurality of k-mers. 70. The method of embodiment 68, wherein assaying for the presence of the sequence signature comprises aligning the sequence signature to a sequence read of the plurality of sequence reads. 71. The method of embodiment 67, wherein the method further comprises removing a nucleic acids encoding a non-target nucleic acid from the sample prior to obtaining sequence information. 72. The method of embodiment 71, wherein the non-target nucleic acid encodes 16S RNA. 73. The method of embodiment 71, wherein the heterogeneous microbial sample is obtained from a host and the non-target nucleic acid encodes a host sequence. 74. The method of embodiment 54, wherein the heterogeneous microbial sample is obtained from a subject. 75. The method of embodiment 74, wherein the subject is human. 76. The method of embodiment 74, wherein the heterogeneous microbial sample comprises earwax, sweat, breast milk, hair, blood, bile, cerebrospinal fluid, lymphatic fluid, semen, vaginal discharge, menstrual fluid, feces, sputum, urine, saliva, secretions from open wounds, secretions from the eye, skin tissue, a skin biopsy, subcutaneous tissue, muscle tissue, adipose tissue, and a combination thereof. 77. The method of embodiment 76, wherein the heterogeneous microbial sample comprises feces. 78. The method of embodiment 54, wherein the heterogeneous microbial sample comprises soil.

79. A non-transitory computer-readable storage media encoded with a computer program including instructions executable by a processor to assay for a presence of a sequence signature in nucleic sequences obtained from a heterogeneous microbial sample informative of a taxon, the storage media comprising a database comprising a plurality of sequence signatures informative of taxa, wherein a sequence signature comprises sequence information of an open reading frame informative of at least one taxon at a taxonomic rank selected from a group consisting of microspecies, strain, subspecies, quasispecies, species, genus, family, order, class, and phylum; and wherein the plurality of sequence signatures are binned by taxonomic rank such that a non-partitioned paired-end read can be identified as comprising a sequence specific to a sequence signature corresponding to a taxon. 80. The storage media of embodiment 79, wherein the sequence signature is represented only once in the database at a taxonomic rank. 81. The storage media of embodiment 79, wherein the sequence signature is at least 24 nucleotides long. 82. The storage media of embodiment 79, wherein the sequence signature is at least 30 nucleotides long. 83. The storage media of embodiment 79, wherein the database does not comprise a sequence signature from a host genome. 84. The storage media of embodiment 83, wherein the host genome is a human genome. 85. The storage media of embodiment 79, wherein the database does not comprise a sequence signature encoding at least a portion of a bacterial ribosomal RNA. 86. The storage media of embodiment 85, wherein the ribosome RNA comprises 16S RNA. 87. A data storage and retrieval system for generating a metagenomics database comprising: a memory; a central processing unit; a software module configured to place a copy of genomic sequences corresponding to open reading frames for a plurality of microorganisms into the memory at a plurality of taxonomic ranks; a software module configured to identify a common genome segment that is common to at least two genomes belonging to microorganisms that have different taxa at a taxonomic rank; and a software module configured to remove the common genome segment from the copy of the genomic sequence at the taxonomic rank, wherein removing the common genome segment improves the performance of a system using the metagenomics database by reducing the resources necessary for operating the database. 88. The data storage and retrieval system of embodiment 87, further comprising a software module configured to generate a sequence signature, the software module comprising means for identifying sequences that are common to at least two genomes belonging to microorganisms that have the same taxonomic name at a taxonomic rank. 89. The data storage and retrieval system of embodiment 87, further comprising a software module configured to generate a sequence signature, the software module comprising means for identifying sequences that are unique to a genome belonging to a microorganism that has a taxon at a taxonomic rank. 90. The data storage and retrieval system of embodiment 87, further comprising a software module configured to remove duplicate genomes from the memory such that no genome is represented more than once. 91. The data storage and retrieval system of embodiment 87, further comprising a software module configured to identify sequences that do not encode at least a portion of an open reading frame. 92. The data storage and retrieval system of embodiment 91, further comprising a software module configured to remove sequences that do not encode at least a portion of an open reading frame.

93. A method for generating a metagenomics database comprising placing a copy of genomic sequences for a plurality of microorganisms into a memory of a computer at a plurality of taxonomic ranks; identifying a genome segment that is unique to a taxon comprising at least one microorganism of the plurality of microorganisms; and retaining the genome segment from the copy of the genomic sequence at the taxonomic rank. 94. The method of embodiment 93, wherein the genomic sequences for the plurality of microorganisms comprise open reading frame sequences. 95. The method of embodiment 93, further comprising segmenting the genomic sequences into k-mers and wherein identifying a genome segment that is unique to a taxon comprising at least one microorganism of the plurality of microorganisms comprises identifying a k-mer that is unique to a taxon comprising at least one microorganism of the plurality of microorganisms. 96. The method of embodiment 95, wherein the k-mers have a length of 24. 97. The method of embodiment 95, wherein the k-mers have a length of 30. 98. The method of embodiment 95, wherein a sequence signature comprises the k-mer that is unique to a taxon comprising at least one microorganism of the plurality of microorganisms. 99. The method of embodiment 95, further comprising assembling the retained genome segments into a contig, wherein the contig comprises a sequence signature. 100. The method of embodiment 93, further comprising identifying a genome segment that is not unique to a taxon at a taxonomic rank and removing the genome segment that is not unique from the database at the taxonomic rank. 101. The method of embodiment 93, wherein identifying a genome segment that is unique to a taxon comprising at least one microorganism of the plurality of microorganisms comprises aligning genome segments from different genomes. 102. The method of embodiment 101, wherein the different genomes a plurality of different taxa at the taxonomic rank. 103. The method of embodiment 93, further comprising repeating the method at a plurality of taxonomic ranks.

104. A method for generating a metagenomics database comprising fetching a copy of genomic sequences for a plurality of microorganisms into a memory of a computer at a plurality of taxonomic ranks; identifying a common genome segment that is common to at least two genomes belonging to microorganisms of different taxa at a taxonomic rank; and removing the common genome segment from the copy of the genomic sequence at the taxonomic rank. 105. The method of embodiment 104, wherein common genome segment comprises a k-mer with a given length k, wherein K is any integer between 10 and 100. 106. The method of embodiment 104, wherein removing the common segments reduces an amount of the memory of the computer required to store the database by 15%. 107. The method of embodiment 104, wherein removing the common segments reduces a size of the database by 15%. 108. The method of embodiment 104, wherein removing the common segments improves the responsiveness of the database by 15%. 109. The method of embodiment 104, wherein removing the common segments does not affect the ability of the database to accurately identify microorganisms present in a sample. 110. The method of embodiment 104, further comprising removing from each genome sequence segments corresponding to ribosomal genes. 111. The method of embodiment 104, further comprising removing from each genome sequences common to a host genome. 112. The method of embodiment 111, wherein the host genome is a human genome.

113. A method performed by computer of creating a curated metagenomic database comprising: a) fetching into computer memory genomic sequences for each of a plurality of microorganisms from one or more genome databases to create a collection of genomes; b) removing from the collection genomes representing duplicates of the same microbial strain; and c) labeling each genome in the collection with a taxonomic label at each of a plurality of different taxonomic levels to create a curated metagenomic database. 114. The method of embodiment 105, further comprising removing from each genome in the collection, nucleotide sequences corresponding to bacteriophage nucleotide sequences. 115. The method of embodiment 105, further comprising removing from each genome in the collection, nucleotide sequences corresponding to plasmid nucleotide sequences. 116. The method of embodiment 105, further comprising removing from each genome in the collection, nucleotide sequences corresponding to host nucleotide sequences.

117. A method performed by computer for creating a library of taxonomic signatures comprising: a) providing in computer memory a curated metagenomic database comprising genomes of microorganisms having different taxonomic labels at each of a plurality of different taxonomic levels; b) scanning a genome in the database with a window k nucleotides in length, wherein k is between 10 and 100, e.g., 24, to generate a library of k-mer sequences in each genome; c) removing from the genome a k-mer sequence corresponding to ribosomal genes; d) at a plurality of different taxonomic levels (e.g., kingdom, phylum, class, order, genus, species, strain), identifying k-mer sequences common to a plurality of genomes belonging to microorganisms having different taxonomic labels at the taxonomic level (e.g., belonging to different kingdoms, phyla, classes, orders, genera, species, strains) and removing from the genome the common sequences, thereby leaving in the genome sequences unique to microorganisms having the taxonomic label at the taxonomic level; e) removing from the genome remaining sequences shorter than n nucleotides, wherein n is a number between 20 and 100, wherein remaining sequences represent taxonomic signatures of a label at the taxonomic level. 118. The method of embodiment 117, further comprising removing from the genome a k-mer sequence common to a host genome. 119. The method of embodiment 118, wherein the host genome is a human genome.

120. A method performed by computer for generating an open reading frame library comprising: a) providing a curated metagenomic database comprising genomes of different microorganisms; b) calling open reading frames in each genome of the database; and c) mapping a plurality of called open reading frames to an annotated catalog of metagenomic open reading frames.

121. A method of generating a set of transcriptome sequences comprising genomes of different microorganisms comprising: a) sequencing a transcriptome from mRNA from a sample from a host comprising a plurality of different microorganisms, to generate sequence reads; b) selecting sequence reads for which there is paired-end sequence data; and c) removing sequence reads that align to a reference genome of the host; to provide a set of host-free transcriptome sequences.

122. A method performed by computer for sample analysis comprising: a) providing a set of host-free transcriptome sequences from a sample from a host, wherein the sample comprises polynucleotides from a plurality of different microorganisms; b) aligning the sequences to a library of taxonomic signatures; c) calling a microorganism at one or more taxa as being present in the sample if, at the taxonomic level, at least 25 reads of at least 100 nucleotides and a mismatch rate of no greater than 2% align to the library.

123. A method performed by computer for sample analysis comprising: a) providing a set of host-free transcriptome sequences from a sample from a host, wherein the sample comprises polynucleotides from a plurality of different microorganisms; b) aligning the sequences to a library of taxonomic signatures; c) eliminating from alignment transcriptome sequences wherein a first portion of the transcriptome sequence alignments to a sequence in the library and a second portion of the transcriptome sequence does not align to genomic sequences flanking the aligned sequence in the library; d) calling a microorganism at one or more taxa as being present in the sample if, at taxonomic level, at least 1 read of at least 100 nucleotides and a mismatch rate of no greater than 2% align to the library.

124. A method performed by computer for quantifying microorganisms labeled at one or more taxonomic levels as being present in a microbiome of a sample from a host sample comprising: a) providing a set of host-free transcriptome sequences from a sample from a host, wherein the sample comprises polynucleotides from a plurality of different microorganisms; b) providing a metagenomic open reading frame library and selecting from the library genomes corresponding to one or more taxonomic labels identified in the set of sequences; c) aligning the set of sequences to the metagenomic open reading frame library; d) determining a measure of gene expression for each taxonomic label based on Reads Per Kilobase of transcript per Million mapped reads; and e) outputting, for the sample, a quantitative measure (e.g., percent or relative amount) of microorganisms at one or more taxonomic labels at one or more taxonomic levels, and optionally including relative expression levels of selected genes. 124a. The method of embodiment 124 further comprising, before aligning, assaying the set of sequences for a presence of one or more sequence signatures in the sample informative of one or more taxa. 124b. The method of embodiment 124a wherein assaying is informative for one or more taxa at a plurality of different taxonomic levels.

125. A method of taxonomically classifying organisms in a heterogeneous microbial sample comprising: obtaining a ribonucleic acids from a heterogeneous microbial sample; obtaining sequence information representative of the ribonucleic acids; assaying for a presence of a sequence signature in the heterogeneous microbial sample informative of a taxon; and categorizing the heterogeneous microbial sample as comprising an organism corresponding to the taxon, wherein assaying comprises identifying a genome from the taxon; identifying an open reading frame in the genome; and assaying for a presence of a sequence in the sequence information corresponding to the open reading frame. 126. The method of embodiment 125, further comprising quantifying an amount of the ribonucleic acids corresponding to the open reading frame.

VIII. EXAMPLES

The following examples are included for illustrative purposes only and are not intended to limit the scope of the invention.

Example 1

Microorganism Detection and Relative Abundance Quantitation

Two sequencing libraries of samples #232 and #237 were prepared using standard methods and RNA purified from the ZymoBIOMICS™ Microbial Community Standards (Zymo Research). Libraries were sequenced using an Illumina NextSeq instrument and standard EDGE quality control (QC) was run on the resulting sequences. Sequence reads were then run independently through GOTTCHA metagenomic profiling software, through mOTUs software, or through software that utilizes the methods of the current disclosure. GOTTCHA was run with the default parameter set using the GOTTCHA bacteria/archaea unique reference signature database. The method was run with a minimally optimized set of filter parameters using a novel and custom bacteria unique reference signature database created using the methods of the current invention. The filter parameters were Minimum Reads: 25, Minimum Linear Length: 100 bp, and Maximum Mismatch rate: 2%. The organisms detected and their relative abundance are shown in FIG. 8. Overall GOTTCHA gave rise to four false positive results and zero false negative results, while metagenomic profiling with the present method gave rise two false positives and one false negative result. FIGS. 9 and 10 demonstrate that metagenomic profiling with the present method produces relative abundance results that have a stronger correlation with expected values than metagenomic profiling with GOTTCHA.

Example 2

Signature Generation for Taxonomic Identification

A metagenomics database comprising sequence signatures informative of taxa is generated. Genomes from identified microorganisms are placed into a computer's memory. The species include members of a variety of different strains, species, genera, and families. Known sequences that encode ribosomal RNA are removed from the genomes.

The computer analyzes the genomes to find unique signatures for different taxonomic ranks. The genomes are partitioned into k-mers that are 30 nucleotides long. A genome from the species with the binomial name A. a (generic name and species name) is determined to contain the k-mers Q, R, S, T, U, V, and W. A genome from the species with the name A. b (same genus, different species as A. a) is determined to contain the k-mers Q, R, T, U, V, W, and X. A species with the binomial name C. d (both a different genus and species than A. a and A. b) is determined to contain the k-mers Q, R, T, U, Y, and Z. The species A. a, A. b, and C. d are members of the same family, E.

The computer compares the genomes of A. a and A. b. The computer identifies that k-mers Q, R, T, U, V, and W are common between the species with a different name at a taxonomic rank (e.g., they are different species). These k-mers are removed from the genomes in the database at the species level as non-informative or non-distinguishing of identifying a single species, or redundant between different taxa at the same taxonomic level. The computer identifies k-mer S as unique to species A. a. K-mer S is retained in the database as a signature sequence for species A. a. The computer identifies k-mer X as unique to species A. b. K-mer X is retained in the database as a k-mer signature sequence for species A. b.

The computer compares the genomes of A. a and C. d. The computer identifies that k-mers Q, R, T, and U are common between the species with different names at a taxonomic rank (e.g., they are in different genera). These k-mers are removed from the genomes in the database at the species level and at the genus level as non-informative of identifying a single species or genus. The computer identifies k-mers V and W as unique to genus A. K-mers V and W are retained in the database as k-mer signature sequences for genus A. The computer identifies sequences Y and Z as unique to species C. d. K-mers Y and Z are retained in the database as a k-mer signature sequence for species C. d and genus C.

K-mer signatures are then assembled into longer sequence signatures. The sequence signatures are labeled with the corresponding taxon or taxa from which they originated. Sequence S is a sequence signature informative of both the species A. a and the genus A. Sequence X is a sequence signature informative of both the species A. b and the genus A. Sequence YZ is a sequence signature informative of both the species C. d and the genus C. Sequence VW is a sequence signature informative of the genus A.

The results are output to a database. The database bins sequence signatures by taxonomic rank. The signatures are stored so they can be compared to partitioned or non-partitioned paired-end reads to determine if the paired-end reads share sequence specific to a sequence signature with a taxon. Because non-informative or non-distinguishing sequences are removed from the database at corresponding taxonomic levels, the database is smaller than a database including the full length of each genome for each identified microorganism. This results in significant performance improvements over full-length genomic databases.

Example 3

Signature Generation Using Open Reading Frames

A metagenomics database comprising sequence signatures informative of taxa is generated. Genomes from identified microorganisms are placed into a computer's memory. The species include members of a variety of different strains, species, genera, and families. The computer analyzes the genomes for open reading frames. Sequences that correspond to open reading frames are retained and sequences that do not correspond to open reading frames are removed from the database. Sequence signatures for different taxonomic ranks are generated and the results are output as a database as described in Example 2. This results in a database containing open reading frame sequence signatures.

Because non-informative sequences are removed from the database at corresponding taxonomic levels, the database is smaller than a database including the full length of each genome for each identified microorganism. This results in significant performance improvements over full-length genomic databases.

Example 4

Analyzing the Microbiome of an Individual

A stool sample is collected from a human subject and analyzed. Ribonucleic acids are isolated from the sample and other substances, including DNA, are removed. Nucleic acid probes are used to remove RNA molecules encoding sequences that are not informative of microbiome characteristics. These include human RNA and 16s microbial RNA. The process of removing these RNA molecules enriches the remaining sample for sequences that contain sequence signatures.

The RNA is then reverse transcribed into DNA. Adapters are added to the ends of the DNA molecules. The adapters contain sequencing primer binding sites and sample-specific barcodes. The sample is then sequenced along with other samples containing different sample-specific barcodes using an Illumina sequencing by synthesis sequencer. The machine obtains paired-end reads with each read approximately 100 nucleotides long from both ends. The paired-end reads are segregated by sample specific barcode. The reads corresponding to the human subject's sample are processed for further analysis.

The sequences are checked against the database of signatures generated in Example 2 using a BWA alignment tool. In this method, the full-length of each paired-end is aligned to the sequence signatures to find a match. Taxa are identified using signature sequences corresponding to the paired-end reads.

Example 5

Analyzing the Biochemical Activity of a Microbial Sample

A stool sample is collected from a human subject and analyzed according to Example 4. Open reading frames are identified in genomes from the taxa identified in Example 4. The paired-end reads are then aligned to the open reading frames of the identified taxa. A biochemical activity is identified as present in the sample when an open reading frame found in the sample encodes a protein associated with a particular function or pathway. Sequence VW maps to an ORF known to be involved in butyrate production. Thus, it is concluded that butyrate production is a biochemical activity present in the sample.

Example 6

Quantification of Biochemical Activity

A stool sample is collected from a human subject and analyzed according to Examples 4 and 5. The paired-end reads are aligned to open reading frames from the detected taxa and an average depth of coverage is calculated for the detected open reading frames. The average depth of coverage is the observed depth of aligned reads over the length an ORF. The average is then normalized over the depth of all ORFs observed in the sample. The ORF associated with sequence VW and butyrate coverage in Example 5 has a length of 1,000 base pairs. 10,000 base pairs of aligned reads map to the ORF, yielding an average of 10× coverage. Sequence XY is found to map to an ORF known to be involved in antibiotic resistance. This ORF has a length of 1,500 base pairs. 30,000 base pairs of aligned reads map to the ORF, yielding an average of 20× coverage. Thus, it is concluded that the relative expression of the antibiotic resistance ORF is twice as high as the expression of the butyrate ORF.

Example 7

Determination of a Suitable Antibiotic

A sample is collected from a human subject suffering from an infection. Ribonucleic acids are isolated from the sample and other substances, including DNA, are removed. Nucleic acid probes are used to remove RNA molecules encoding sequences that are not informative of microbiome characteristics. These include human RNA and 16s microbial RNA. The process of removing these RNA molecules enriches the remaining sample for sequences that contain sequence signatures.

The RNA is then reverse transcribed into DNA. Adapters are added to the ends of the DNA molecules. The adapters contain sequencing primer binding sites and sample-specific barcodes. The sample is then sequenced along with other samples containing different sample-specific barcodes using an Illumina sequencing by synthesis sequencer. The machine obtains paired-end reads with each read approximately 100 nucleotides long from both ends. The paired-end reads are segregated by sample specific barcode. The reads corresponding to the human subject's sample are processed for further analysis.

Taxa are identified for microbes present in the sample using the methods described in Example 4. The paired-end reads are then aligned to the open reading frames encoding genes known to be associated with antibiotic resistance from the identified taxa. An antibiotic resistance gene is identified as present in the sample when an open reading frame found in the sample matches an open reading frame associated with a particular antibiotic resistance function or pathway. Sequence S is detected in the sample and known to be associated with an ORF encoded by bacterial species A. a that exhibits resistance to amoxicillin. It is known that A. a is not resistant to macrolides. A recommendation is made to administer erythromycin to the patient.

Example 8

Comparison of Using Full-Length Sequencing Reads and Partitioned Reads

A stool sample is collected from a human subject and analyzed. Ribonucleic acids are isolated from the sample and other substances, including DNA, are removed. Nucleic acid probes are used to remove RNA molecules encoding sequences that are not informative of microbiome characteristics. These include human RNA and 16s microbial RNA. The process of removing these RNA molecules enriches the remaining sample for sequences that contain sequence signatures.

The RNA is then reverse transcribed into DNA. Adapters are added to the ends of the DNA molecules. The adapters contain sequencing primer binding sites and sample-specific barcodes. The sample is then sequenced along with other samples containing different sample-specific barcodes using an Illumina sequencing by synthesis sequencer. The machine obtains paired-end reads with each read approximately 150 nucleotides long from both ends. The paired-end reads are segregated by sample specific barcode. The reads corresponding to the human subject's sample are processed for further analysis by two different methods.

In a first method, taxa are identified for the paired-end reads using a method in accordance with this disclosure. Contiguity information for each paired-end read is retained. As a result, a first end of the paired-end reads is identified as belonging to the same molecule, and therefore originating from the same cell, as the second end of the paired-end read. Each end is aligned to the sequence signature database generated in Example 2 and analyzed for the presence of potential sequence signatures. In a first paired-end read, a first end is identified as belonging to *Bacillus subtilis*. The second end from the same paired-end read is identified as belonging to *Bacillus,* but a species cannot be identified. Both ends are identified as originating from a *Bacillus subtilis* bacterium using the more informative sequence signature detected of the two. This is because both reads are present on the same molecule and originated from the same cell even if the sequence signatures detected in each read vary in specificity.

In a second method, taxa for the same paired-end read analyzed above are identified analyzed using GOTTCHA in parallel. The reads are partitioned into non-overlapping k-mers that are 30 nucleotides long. Contiguity information is not retained for each 30-mer from the original sequence read. The 30-mers are independently aligned to the sequence signature database generated in Example 2 and sequence signatures determined, where appropriate, for each independent 30-mer. A first 30-mer is identified as containing a *Bacillus* signature. A second 30-mer is identified as containing a Bacillaceae family signature. A third 30-mer is identified as containing a *Bacillus subtilis* signature. Because contiguity information is not retained, it is unclear if the three signatures arose from one, two, or three different organisms.

The results of the methods are compared. It is determined that the first method using a method in accordance with this disclosure is more accurate than the second method using GOTTCHA. The first method more accurately identifies the origins of paired-end reads. This is because the entire paired-end read is classified according to the most informative signature within the molecule using the first method. The first method assigns the entire paired-end read to a single taxon, whereas the second method leaves room for the possibility that sequence signatures at the genus and family taxonomic ranks are from unknown organisms or known organisms with overlapping sequence signatures.

It is determined that the use of non-partitioned reads is also more accurate because the increase in sequence length allows for the assessment and comparison of a longer sequence to the sequence signature database. The use of non-partitioned reads allows for the detection of sequence signatures containing differences that are more than 30 nucleotides apart, whereas the use of partitioned reads requires the unique signature to be present in a smaller sequence.

The first method also more accurately quantifies the number of sequences arising from a single taxon as a single paired-end read is only counted once based on the best sequence signature found in the entire read. The first method identified the entire paired-end read as belonging to *B. subtilis*. The second method determined that members of three different taxonomic ranks were present, but could not determine if the members were from the same organism or template molecule. Thus, the results show that partitioning the reads can lead to multiple counts within a single taxon or counts at multiple taxonomic ranks within a single hierarchy even if signatures map back to the same template molecule. Furthermore, the increase in accuracy allows more accurate counting and quantification of organisms present in the sample.

It is determined that the use of non-partitioned reads also allows for several performance increases. Once a sequence is identified as belonging to a more specific taxon, the sequence does not need to be aligned to higher, less specific taxonomic levels. This applies to the entire read, whereas k-mers are analyzed individually regardless of contiguity information. Each k-mer requires independent generation, independent analysis, and independent storage. Thus, the amount of data processing and storage is improved when using paired-end reads instead of k-mers. In contrast, the partitioned 3-mers are classified independently of one another and do not take contiguity data into account. Thus, a sequence signature for a k-mer is informative only for that k-mer.

By using the entire paired-end read, the system can complete the analysis using fewer alignments than breaking up the sequence into multiple k-mers. The use of paired-end reads instead of k-mers allows the system to detect and store fewer hits per read.

Example 9

Quantification of Biochemical Activity

A stool sample is collected from a human subject and analyzed. Ribonucleic acids are isolated from the sample and other substances, including DNA, are removed. Nucleic acid probes are used to remove RNA molecules encoding sequences that are not informative of microbiome characteristics. These include human RNA and 16s microbial RNA. The process of removing these RNA molecules enriches the remaining sample for sequences that contain sequence signatures.

The RNA is then reverse transcribed into DNA. Adapters are added to the ends of the DNA molecules. The adapters contain sequencing primer binding sites and sample-specific barcodes. The sample is then sequenced along with other samples containing different sample-specific barcodes using an Illumina sequencing by synthesis sequencer. The machine obtains paired-end reads with each read approximately 150 nucleotides long from both ends. The paired-end reads are segregated by sample specific barcode. The reads corresponding to the human subject's sample are processed for further analysis by two different methods.

Taxa are identified for the paired-end reads using a method in accordance with this disclosure. Contiguity information for each paired-end read is retained. As a result, a first end of the paired-end reads is identified as belonging to the same molecule, and therefore originating from the same cell, as the second end of the paired-end read. Each end is aligned to the sequence signature database generated in Example 2 and analyzed for the presence of potential sequence signatures. In a first paired-end read, a first end is identified as belonging to *Bacillus subtilis*. The second end from the same paired-end read is identified as belonging to *Bacillus*, but a species cannot be identified. Both ends are identified as originating from a *Bacillus subtilis* bacterium using the more informative sequence signature detected of the two. This is because both reads are present on the same molecule and originated from the same cell even if the sequence signatures detected in each read vary in specificity.

In this example, the identified taxa include *Bacillus subtilis*, as described above, and *Lactobacillus acidophilus*, among others.

A new database is generated that includes open reading frames from identified taxa. Genomes for identified taxa, including *Bacillus subtilis* and *Lactobacillus acidophilus*, are pulled from NCBI. The genomes are then scanned to identify open reading frames using ORF Finder or MetaGene ("MetaGene: prokaryotic gene finding from environmental genome shotgun sequence", H. Noguchi, J. Park and T. Takagi Nucleic Acids Research (2006) 34(19):5623-5630).

Identified open reading frames are then mapped to MetaHIT, an annotated catalog of metagenomic open reading frames. Such a catalog can be found at, for example, Li et al., MetaHIT Consortium, "An integrated catalog of reference genes in the human gut microbiome," Nat Biotechnol. 2014 August; 32(8):834-41. doi: 10.1038/nbt.2942. PubMed PMID: 24997786.

The paired-end reads obtained from the cDNA are mapped to the open reading frame database. An average depth of coverage is calculated for the detected open reading frames. The average depth of coverage is the observed depth of aligned reads over the length an ORF. An ORF from *Bacillus subtilis* associated with butyrate production has a length of 1,000 base pairs. 10,000 base pairs of aligned reads map to the ORF, yielding an average of 10× coverage. An ORF from *Lactobacillus acidophilus* associated with lactic acid production has a length of 1,500 base pairs. 30,000 base pairs of aligned reads map to the ORF, yielding an average of 20× coverage. Thus, it is concluded that the relative expression of the ORF from *Lactobacillus acidophilus* is twice as high as the expression of the *Bacillus subtilis* ORF.

All publications and patent applications mentioned in this specification are herein incorporated by reference to the same extent as if each individual publication or patent application was specifically and individually indicated to be incorporated by reference.

While certain embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

The invention claimed is:

1. A method of taxonomically classifying organisms in a heterogeneous microbial sample comprising:
   obtaining ribonucleic acids from a heterogeneous microbial sample from a host;
   reverse transcribing the ribonucleic acids from the heterogeneous microbial sample into cDNA;
   obtaining, in electronic form, metatranscriptomic sequence information representative of the ribonucleic acids by high throughput sequencing of the cDNA, wherein the metatranscriptomic sequence information comprises a plurality of sequence reads;
   determining, at a computer comprising at least one processor and a memory storing at least one program for execution by the at least one processor, a corresponding abundance of each respective microbial taxon in a plurality of microbial taxa in the heterogeneous microbial sample by mapping the plurality of sequence reads to a library of sequence signatures for the plurality of microbial taxon, wherein:
      the plurality of microbial taxa are of the same taxonomic rank,
      the library of sequence signatures is generated from genomes of the microbial taxa and curated by: (i) removing each sequence signature in the library of sequence signatures fewer than 20 nucleotides long, and (ii) removing k-mers, in a distinct set of k-mers determined from the genomes of the microbial taxa, that are present in more than one microbial taxa in the plurality of microbial taxa from each sequence signature in the library of sequence signatures, wherein
      k is an integer between 10 and 100;
   assaying for a presence of a biochemical activity in the heterogenous microbial sample by mapping the plurality of sequence reads to an open reading frame in the library of sequence signatures and identifying a gene associated with the biochemical activity encoded by the open reading frame; and
   using at least the corresponding abundance of each respective microbial taxon in the plurality of microbial taxa to characterize a microbial composition of the heterogenous microbial sample.

2. The method of claim 1, wherein the determining a corresponding abundance of the respective microbial taxon comprises assaying for respective sequences in the plurality of sequence reads corresponding to the respective microbial taxon.

3. The method of claim 2, wherein the respective sequences comprise nucleotide sequences unique to the respective microbial taxon at the taxonomic rank.

4. The method of claim 2, wherein determining the corresponding abundance of the respective microbial taxon comprises determining a depth of coverage for the respective sequences corresponding to the respective microbial taxon relative to a total depth of coverage for sequences present in the sample.

5. The method of claim 1, wherein the corresponding abundance is determined using a number of reads per kilobase corresponding to the respective microbial taxon per million mapped reads.

6. The method of claim 1, further comprising assaying the metatranscriptomic sequence information representative of the ribonucleic acids for a presence of a gene encoded by a genome of the respective microbial taxon.

7. The method of claim 6, wherein assaying the metatranscriptomic sequence information representative of the ribonucleic acids for a presence of a gene encoded by a genome of the respective microbial taxon comprises:
  identifying a genome from the respective microbial taxon;
  identifying a gene in the genome; and
  assaying for a presence of a sequence in the metatranscriptomic sequence information corresponding to the gene.

8. The method of claim 6, further comprising quantifying sequences corresponding to the gene encoded by the genome of the respective microbial taxon.

9. The method of claim 1, further comprising removing non-target ribonucleic acids from the sample prior to obtaining sequence information.

10. The method of claim 9, wherein the non-target ribonucleic acids comprise ribosomal RNAs.

11. The method of claim 9, wherein the non-target ribonucleic acids comprise host RNAs.

12. The method of claim 1, wherein sequencing the cDNA comprises obtaining a plurality of single-end sequence reads.

13. The method of claim 1, wherein sequencing the cDNA comprises obtaining a plurality of paired-end sequence reads.

14. The method of claim 1, wherein the determining the corresponding abundance of the respective microbial taxon does not comprise partitioning a respective sequence read of the plurality of sequence reads into a plurality of k-mers.

15. The method of claim 1, wherein the host is human.

16. The method of claim 1, wherein the heterogeneous microbial sample comprises earwax, sweat, breast milk, hair, blood, bile, cerebrospinal fluid, lymphatic fluid, semen, vaginal discharge, menstrual fluid, feces, sputum, urine, saliva, secretions from open wounds, secretions from the eye, skin tissue, a skin biopsy, subcutaneous tissue, muscle tissue, adipose tissue, and a combination thereof.

17. The method of claim 16, wherein the heterogeneous microbial sample comprises feces.

18. The method of claim 9, wherein removing comprises hybridizing the one or more RNAs with a nucleic acid probe.

19. The method of claim 1, wherein the metatranscriptomic sequence information comprises thousands of sequence reads.

20. The method of claim 19, further comprising outputting, for each respective microbial taxon in the plurality of microbial taxa, a corresponding quantity of the respective microbial taxon in the heterogenous microbial sample.

21. The method of claim 1, further comprising outputting a corresponding quantity of the biochemical activity corresponding to the gene in the heterogenous microbial sample.

22. The method of claim 1, wherein the processor is configured to receive at least one input file comprising sequence information and at least one database comprising taxonomic information and gene information.

23. The method of claim 10, wherein the ribosomal RNA comprises 16S RNA.

24. The method of claim 1, wherein the ribonucleic acids comprise one or more of bacterial RNA, viral RNA and plasmid RNA.

25. The method of claim 1, wherein the gene encodes for an enzyme.

26. The method of claim 1, wherein the gene is involved in a pathway related to breaking down polysaccharides.

27. The method of claim 1, wherein the gene is involved in a production of acetic acid, propionic acid, butyric acid, biotin or folate.

28. The method of claim 1, wherein the gene is involved in absorption of minerals.

29. The method of claim 1, wherein the plurality of microbial taxa include one or more of: Bacillus subtilis, Clostridium botulinum, Enterococcus faecalis, Escherichia coli, Lactobacillus buchneri, Lactobacillus fermenutm, Lactobacillus johnsonii, Listeria monocytogenes, Pseudomonas aeruginosa, Salmonella enterica, and Staphylococcus aureus.

30. The method of claim 1, wherein the heterogeneous microbial sample is obtained from a host suffering from an infection, the gene is an antibiotic resistance gene for a particular antibiotic, and the method further comprises, when the assaying identifies a presence of the antibiotic resistance gene, administering to the host a treatment other than the particular antibiotic.

31. The method of claim 1, wherein the mapping the plurality of sequence reads to the library of sequence signatures comprises retaining contiguity information for the plurality of sequence reads without partitioning the sequence reads into k-mers.

32. The method of claim 31, wherein the metatranscriptomic sequence information consists of a plurality of paired-end sequence reads obtained from the sequencing.

33. The method of claim 1, wherein the removing each sequence signature in the library of sequence signatures fewer than 20 nucleotides long reduces a number of alignments required for the mapping by 10%, 20%, 40%, 60%, 80%, or 90%.

* * * * *